(12) United States Patent
Bo et al.

(10) Patent No.: US 8,729,074 B2
(45) Date of Patent: May 20, 2014

(54) INHIBITORS OF PI3 KINASE

(75) Inventors: Yunxin Y. Bo, Thousand Oaks, CA (US); Longbin Liu, Thousand Oaks, CA (US); Nobuko Nishimura, West Hills, CA (US); Mark H. Norman, Thousand Oaks, CA (US); Aaron C. Siegmund, Ventura, CA (US); Nuria A. Tamayo, Newbury Park, CA (US); Kevin C. Yang, San Gabriel, CA (US)

(73) Assignee: Amgen Inc., Thousand Oaks, CA (US)

( * ) Notice: Subject to any disclaimer, the term of this patent is extended or adjusted under 35 U.S.C. 154(b) by 240 days.

(21) Appl. No.: 13/257,582

(22) PCT Filed: Mar. 19, 2010

(86) PCT No.: PCT/US2010/027929
§ 371 (c)(1),
(2), (4) Date: Nov. 21, 2011

(87) PCT Pub. No.: WO2010/108074
PCT Pub. Date: Sep. 23, 2010

(65) Prior Publication Data
US 2012/0071474 A1   Mar. 22, 2012

Related U.S. Application Data

(60) Provisional application No. 61/162,144, filed on Mar. 20, 2009.

(51) Int. Cl.
*A61K 31/535*   (2006.01)

(52) U.S. Cl.
USPC ............ 514/233.2; 514/259.1; 514/300; 514/259.5; 514/248; 544/127; 544/281; 544/236; 546/121

(58) Field of Classification Search
USPC ............ 514/233.2, 259.1, 300, 259.5, 248; 544/127, 281, 236; 546/121
See application file for complete search history.

(56) References Cited

FOREIGN PATENT DOCUMENTS

| WO | WO02/076983 A1 | 10/2002 |
|---|---|---|
| WO | WO03/015366 A2 | 6/2003 |
| WO | WO03/092595 A2 | 11/2003 |
| WO | WO03/099817 A1 | 12/2003 |
| WO | WO2004/099127 A1 | 11/2004 |
| WO | WO2006/039718 A2 | 4/2006 |
| WO | WO2006/046031 A1 | 5/2006 |
| WO | WO2007/058873 A2 | 5/2007 |
| WO | WO2007/076092 A2 | 7/2007 |
| WO | WO2007/095588 A1 | 8/2007 |
| WO | WO2007/132171 A1 | 11/2007 |
| WO | WO2007/135398 A1 | 11/2007 |
| WO | WO2008/014219 A2 | 1/2008 |
| WO | WO2008/032060 A1 | 3/2008 |
| WO | WO2008/032064 A1 | 3/2008 |
| WO | WO2008/032072 A1 | 3/2008 |
| WO | WO2008/032077 A1 | 3/2008 |
| WO | WO2008/032086 A1 | 3/2008 |
| WO | WO2008/032089 A1 | 3/2008 |
| WO | WO2008/032091 A1 | 3/2008 |
| WO | WO2008/037477 A1 | 4/2008 |
| WO | WO2008/052733 A1 | 5/2008 |
| WO | WO2008/078091 A1 | 7/2008 |
| WO | WO2008/133192 A1 | 11/2008 |
| WO | WO2008/138834 A1 | 11/2008 |
| WO | WO2008/138889 A2 | 11/2008 |
| WO | WO2009/008748 A1 | 1/2009 |
| WO | WO2009/010530 A1 | 1/2009 |
| WO | WO2009/013348 A2 | 1/2009 |
| WO | WO2009/017822 A2 | 2/2009 |
| WO | WO2009/021990 A1 | 2/2009 |
| WO | WO2009/055418 A1 | 4/2009 |
| WO | WO2009/085230 A1 | 7/2009 |
| WO | WO2009/115517 A2 | 9/2009 |
| WO | WO2009/120094 A2 | 10/2009 |
| WO | WO2009/133127 A1 | 11/2009 |
| WO | WO2009/150240 A1 | 12/2009 |
| WO | WO2009/155121 A2 | 12/2009 |
| WO | WO2010/007099 A1 | 1/2010 |
| WO | WO2010/016005 A1 | 2/2010 |
| WO | WO2010/036380 A1 | 4/2010 |

(Continued)

OTHER PUBLICATIONS

Masahiko Hayakawa, "Synthesis and biological evaluation of imidazo[1,2-α]pyridine derivatives as novel PI3 kinase p110α inhibitors," Bioorganic & Medicinal Chemistry, vol. 15, (2007), pp. 403-412.

Masahiko Hayakawa, "Synthesis and biological evaluation of pyrido[3',2':4,5]furo [3,2-*d*]pyrimidine derivatives as novel PI3 kinase p110α inhibitors," Bioorganic & Medicinal Chemistry Letters, vol. 17, (2007), pp. 2438-2442.

Motosuke Yamanaka, "Imidazo[1,2-α]pyridines. I. Synthesis and Inotropic Activity of New 5-Imidazo[1,2-α]pyridinyl-2(1*H*)-pyridinone Derivatives," Chemical & Pharmaceutical Bulletin, vol. 39(6), pp. 1556-1567.

(Continued)

*Primary Examiner* — Jason Sims
*Assistant Examiner* — Ibrahim D Bori
(74) *Attorney, Agent, or Firm* — Todd M. Crissey

(57) ABSTRACT

The present invention relates to compounds of Formula I, II or III or a pharmaceutically acceptable salt thereof;

I

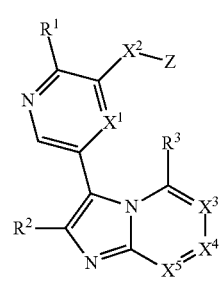

methods of treating diseases or conditions, such as cancer, using the compounds; and pharmaceutical compositions containing the compounds, wherein the variables are as defined herein.

2 Claims, No Drawings

(56) References Cited

FOREIGN PATENT DOCUMENTS

| WO | WO2010/074586 A1 | 7/2010 |
| WO | WO2010/100144 A1 | 9/2010 |
| WO | WO2010/119264 A1 | 10/2010 |
| WO | WO2010/126895 A1 | 11/2010 |
| WO | WO2010/133534 A1 | 11/2010 |

OTHER PUBLICATIONS

International Search Report & Written Opinion, PCT/US2010/027929, Issued Sep. 27, 2010, pp. 1-14.

INHIBITORS OF PI3 KINASE

CROSS-REFERENCE TO RELATED APPLICATIONS

This application is a 35 U.S.C. §371 filing of PCT Application No. PCT/US2010/27929, filed Mar. 19, 2010, which claims priority of U.S. Provisional Application No. 61/162,144, filed Mar. 20, 2009, the contents of which are incorporated by reference herein in their entirety.

FIELD OF THE INVENTION

The present invention relates to compounds that inhibit phosphoinositide 3-kinase (PI3K); methods of treating diseases or conditions, such as cancer, using the compounds; and pharmaceutical compositions containing the compounds.

BACKGROUND OF THE INVENTION

PI3 kinases are a family of lipid kinases that have been found to play a key role in the regulation of many cellular processes including proliferation, survival, carbohydrate metabolism, and motility. PI3Ks are considered to have an important role in intracellular signal transduction. In particular, the PI3Ks generate and convey signals that have important roles in cancer. PI3Ks are ubiquitously expressed, are activated by a high proportion of cell surface receptors, especially those linked to tyrosine kinases, and influence a variety of cellular functions and events. Although some PI3K activity is likely to be essential for cellular health, PI3Ks are a diverse group of enzymes for which there is increasing evidence of functional specialization. This opens up the possibility of developing isoform-selective inhibitors that can be used to treat cancer.

The primary enzymatic activity of PI3K is the phosphorylation of inositol lipids (phosphoinositides) on the 3-position of the inositol headgroup. PI3 kinases catalyze the addition of phosphate to the 3'-OH position of the inositol ring of inositol lipids generating phosphatidyl inositol monophosphate, phosphatidyl inositol diphosphate and phosphatidyl inositol triphosphate.

There are a total of eight mammalian PI3Ks, which have been divided into three main classes on the basis of sequence homology, in vitro substrate preference, and method of activation and regulation. Enzymes of a first class (Class I) have a broad substrate specificity and phosphorylate phosphatidylinositiol (PtdIns), PtdIns(4)P and PtdIns(4,5)P$_2$. Class I PI3 kinases include mammalian p110α, p110β, p110δ and p110γ. Different members of the PI3-kinase family generate different lipid products. To date, four 3-phosphorylated inositol lipids have been identified in vivo. These lipids are bound by proteins that contain the appropriate lipid recognition module and which either act as effectors or transmit the PI3K signal onwards. The most familiar form of PI3K is a heterodimeric complex, consisting of a 110 kDa catalytic subunit now known as p110α and an 85 kDa regulatory/adapter subunit, p85α.

Phosphatidylinositol 3-kinase-alpha (PI3Kα), a dual specificity lipid and protein kinase, is composed of an 85 kDa regulatory subunit and a 110 kDa catalytic subunit. The protein includes a catalytic subunit, which uses ATP to phosphorylate PtdIns, PtdIns(4)P and PtdIns(4,5)P$_2$. PTEN, a tumor suppressor, can dephosphorylate phosphatidylinositol (3,4,5)-trisphosphate (PIP3), the major product of PI3 kinase Class I. PIP3, in turn, is required for translocation of protein kinase B (AKT1, PKB) to the cell membrane, where it is phosphorylated and activated by upstream kinases. The effect of PTEN on cell death is mediated through the PI3Kα/AKT1 pathway.

PI3Kα has been implicated in the control of cytoskeletal reorganization, apoptosis, vesicular trafficking and proliferation and differentiation processes. Increased copy number and expression of the p110α gene (PIK3CA) is associated with a number of cancers such as ovarian cancer, cervical cancer, breast cancer, colon cancer, rectal cancer, endometrial cancer, stomach cancer, liver cancer, lung cancer, thyroid cancer, acute myelogenous leukemia (AML), chronic myelogenous leukemia (CML), and glioblastomas. In view of the important role of PI3Kα in biological processes and disease states, inhibitors of this protein kinase are desirable. The present invention provides PI3K inhibitors, particularly PI3Kα inhibitors, which are useful for treating PI3Kα-mediated diseases and conditions.

SUMMARY OF THE INVENTION

In one embodiment, the present invention provides compounds of Formula I

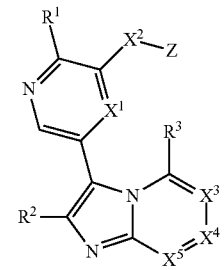

and the pharmaceutically acceptable salts thereof,
wherein $X^1$ is N or CR;
$R^1$ is hydrogen, halo, —CF$_3$, —C$_{1-6}$alkyl, —C$_{2-6}$alkenyl, —C$_{2-6}$alkynyl, —OC$_{1-6}$alkyl, —SC$_{1-6}$alkyl, or —CN, wherein the —C$_{1-6}$alkyl, —C$_{2-6}$alkenyl, or —C$_{2-6}$alkynyl are substituted by 0, 1, 2 or 3 substituents independently selected from —C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^2$ is hydrogen, halo, —CF$_3$, —C$_{1-6}$alkyl, —C$_{2-6}$alkenyl, —C$_{2-6}$alkynyl, —OC$_{1-6}$alkyl, or —CN, wherein the —C$_{1-6}$alkyl, —C$_{2-6}$alkenyl, or —C$_{2-6}$alkynyl are substituted by 0, 1, 2 or 3 substituents independently selected from —C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, or —NR$^a$C$_{2-6}$alkylOR$^a$;

X$^2$ is —N(R$^a$)S(=O)$_2$(CR$^a$R$^a$)$_n$—, —N(R$^a$)C(=O)(CR$^a$R$^a$)$_n$—, —O(CR$^a$R$^a$)$_n$—, —(CR$^a$R$^a$)$_n$O—, —(CR$^a$R$^a$)$_n$S(=O)$_m$—, —(CR$^a$R$^a$)$_n$N(R$^a$)—, —N(R$^a$)(CR$^a$R$^a$)$_n$—, —S(O)$_m$(CR$^a$R$^a$)$_n$—, —N(R$^a$)(CR$^a$R$^a$)$_n$—, —S(=O)$_2$N(R$^a$)(CR$^a$R$^a$)$_n$—, —N(R$^a$)C(=O)O(CR$^a$R$^a$)$_n$—, —N(R$^a$)C(=O)NR$^a$(CR$^a$R$^a$)$_n$—, —N(R$^a$)C(=NR$^a$)NR$^a$(CR$^a$R$^a$)$_n$—, —OC(=O)NR$^a$(CR$^a$R$^a$)$_n$—, or —N(R$^a$)S(=O)$_2$NR$^a$(CR$^a$R$^a$)$_n$—;

X$^3$ and X$^4$ are independently N or CR$^c$;

X$^5$ is N or CR$^d$;

R$^d$ is hydrogen, C$_{1-4}$haloalkyl, halo or —C$_{1-6}$alkyl;

each R$^3$ and R$^c$ are independently hydrogen, C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, or —C$_{2-6}$alkynyl, wherein the —C$_{1-6}$alkyl, —C$_{2-6}$alkenyl, or —C$_{2-6}$alkynyl are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Z is hydrogen, —C$_{1-6}$alkyl, —C$_{2-6}$alkenyl, —C$_{2-6}$alkynyl, —C(=O)R$^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C$_{1-6}$alkyl, —C$_{2-6}$alkenyl, —C$_{2-6}$alkynyl, or ring are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R is independently hydrogen, C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, —C$_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C$_{1-6}$alkyl, —C$_{2-6}$alkenyl, —C$_{2-6}$alkynyl, or ring are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, N(R$^a$)(CR$^a$R$^a$)$_n$—Y, —(CR$^a$R$^a$)$_n$Y, or —(CR$^a$R$^a$)$_n$OR$^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^1$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R$^a$ is independently hydrogen or R$^b$;

each R$^b$ is independently phenyl, benzyl or C$_{1-6}$alkyl, wherein the phenyl, benzyl or C$_{1-6}$alkyl is substituted by 0, 1, 2 or 3 substituents independently selected from halo, C$_{1-4}$alkyl, C$_{1-3}$haloalkyl, —OC$_{1-4}$alkyl, —NH$_2$, —CN, —NHC$_{1-4}$alkyl, or —N(C$_{1-4}$alkyl)$_2$;

each n is independently 0, 1, 2, or 3; and each m is independently 0, 1, or 2.

In another embodiment of the compounds of Formula I, or the pharmaceutically acceptable salts thereof, either alone or in combination with any of the above or below embodiments, R$^1$ is hydrogen, halo, C$_{1-6}$alkyl, —OC$_{1-6}$alkyl, or —SC$_{1-6}$alkyl.

In another embodiment of the compounds of Formula I, or the pharmaceutically acceptable salts thereof, either alone or in combination with any of the above or below embodiments, $R^1$ is hydrogen, chlorine, methyl or —Omethyl.

In another embodiment of the compounds of Formula I, or the pharmaceutically acceptable salts thereof, either alone or in combination with any of the above or below embodiments, $X^2$ is —N($R^a$)S(=O)$_2$(C$R^a R^a$)$_n$—, —N($R^a$)S(=O)$_2$N$R^a$(C$R^a R^a$)$_n$—, or —O(C$R^a R^a$)$_n$—.

In another embodiment of the compounds of Formula I, or the pharmaceutically acceptable salts thereof, either alone or in combination with any of the above or below embodiments, $X^2$ is —NHS(=O)$_2$— or —O—.

In another embodiment of the compounds of Formula I, or the pharmaceutically acceptable salts thereof, either alone or in combination with any of the above or below embodiments, Z is —C$_{1-6}$alkyl or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2R^b$, —OC$_{2-6}$alkylN$R^a R^a$, —OC$_{2-6}$alkylO$R^a$, —S$R^a$, —S(=O)$R^b$, —S(=O)$_2R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2R^b$, —N($R^a$)S(=O)$_2$N$R^a R^a$, —N$R^a$C$_{2-6}$alkylN$R^a R^a$ or —N$R^a$C$_{2-6}$alkylO$R^a$.

In another embodiment of the compounds of Formula I, or the pharmaceutically acceptable salts thereof, either alone or in combination with any of the above or below embodiments, Z is methyl or phenyl substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2R^b$, —OC$_{2-6}$alkylN$R^a R^a$, —OC$_{2-6}$alkylO$R^a$, —S$R^a$, —S(=O)$R^b$, —S(=O)$_2R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2R^b$, —N($R^a$)S(=O)$_2$N$R^a R^a$, —N$R^a$C$_{2-6}$alkylN$R^a R^a$ or —N$R^a$C$_{2-6}$alkylO$R^a$.

In another embodiment of the compounds of Formula I, or the pharmaceutically acceptable salts thereof, either alone or in combination with any of the above or below embodiments, Z is methyl; or phenyl substituted with fluorine.

In another embodiment of the compounds of Formula I, or the pharmaceutically acceptable salts thereof, either alone or in combination with any of the above or below embodiments, $X^1$ is —CR.

In another embodiment of the compounds of Formula I, or the pharmaceutically acceptable salts thereof, either alone or in combination with any of the above or below embodiments, $X^1$ is —CH.

In another embodiment of the compounds of Formula I, or the pharmaceutically acceptable salts thereof, either alone or in combination with any of the above or below embodiments, $R^1$ is hydrogen, halo, C$_{1-6}$alkyl, —OC$_{1-6}$alkyl, or —SC$_{1-6}$alkyl;

$X^2$ is —N($R^a$)S(=O)$_2$(C$R^a R^a$)$_n$—, —N($R^a$)S(=O)$_2$N$R^a$(C$R^a R^a$)$_n$—, or —O(C$R^a R^a$)$_n$—;

Z is —C$_{1-6}$alkyl or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2R^b$, —OC$_{2-6}$alkylN$R^a R^a$, —OC$_{2-6}$alkylO$R^a$, —S$R^a$, —S(=O)$R^b$, —S(=O)$_2R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2R^b$, —N($R^a$)S(=O)$_2$N$R^a R^a$, —N$R^a$C$_{2-6}$alkylN$R^a R^a$ or —N$R^a$C$_{2-6}$alkylO$R^a$; and $X^1$ is —CR.

In another embodiment of the compounds of Formula I, or the pharmaceutically acceptable salts thereof, either alone or in combination with any of the above or below embodiments, $R^2$ is hydrogen or C$_{1-6}$alkyl.

In another embodiment of the compounds of Formula I, or the pharmaceutically acceptable salts thereof, either alone or in combination with any of the above or below embodiments, $X^3$ and $X^4$ are C$R^c$, and $X^5$ is N.

In another embodiment of the compounds of Formula I, or the pharmaceutically acceptable salts thereof, either alone or in combination with any of the above or below embodiments, $X^3$ and $X^4$ are C$R^c$ and $R^c$ is hydrogen, halo or C$_{1-6}$alkyl.

In another embodiment of the compounds of Formula I, or the pharmaceutically acceptable salts thereof, either alone or in combination with any of the above or below embodiments, each $R^3$ is independently hydrogen, halo or C$_{1-6}$alkyl.

In another embodiment of the compounds of Formula I, or the pharmaceutically acceptable salts thereof, either alone or in combination with any of the above or below embodiments, $X^3$ is C$R^c$.

In another embodiment of the compounds of Formula I, or the pharmaceutically acceptable salts thereof, either alone or in combination with any of the above or below embodiments, $X^4$ is N; $X^3$ is C$R^c$; and $X^5$ is C$R^d$.

In another embodiment of the compounds of Formula I, or the pharmaceutically acceptable salts thereof, either alone or in combination with any of the above or below embodiments, $X^3$ is CH.

In another embodiment of the compounds of Formula I, or the pharmaceutically acceptable salts thereof, either alone or in combination with any of the above or below embodiments, $X^2$ is —N($R^a$)S(=O)$_2$(C$R^a R^a$)$_n$— and Z is a saturated, partially saturated or unsaturated 5-, 6- or 7-membered monocyclic ring containing 0, 1, 2, 3 or 4 heteroatoms independently selected from N, O and S.

In another embodiment of the compounds of Formula I, or the pharmaceutically acceptable salts thereof, either alone or in combination with any of the above or below embodiments, $X^2$ is —NHS(=O)$_2$— and Z is selected from

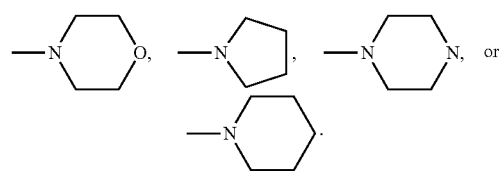

In a second embodiment, the present invention provides compounds of Formula II

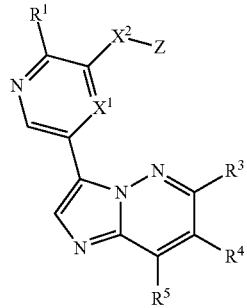

and the pharmaceutically acceptable salts thereof,
wherein $X^1$ is N or CR;
$R^1$ is hydrogen, halo, —$CF_3$, —$C_{1-6}$alkyl, —$C_{2-6}$alkenyl, —$C_{2-6}$alkynyl, —$OC_{1-6}$alkyl, —$SC_{1-6}$alkyl, or —CN, wherein the —$C_{1-6}$alkyl, —$C_{2-6}$alkenyl, or —$C_{2-6}$alkynyl are substituted by 0, 1, 2 or 3 substituents independently selected from —$C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each $R^3$, $R^4$ and $R^5$ are independently selected from hydrogen, $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—$C_{1-6}$alkylN($R^a$)C(=O)O$R^b$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, or —$C_{2-6}$alkynyl, wherein the —$C_{1-6}$alkyl, —$C_{2-6}$alkenyl, or —$C_{2-6}$alkynyl are substituted by 0, 1, 2 or 3 substituents independently selected from $C_{1-8}$alkyl, —$C_{2-6}$alkenyl, —$C_{2-6}$ alkynyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^aR^a$)$_n$Y, or —(C$R^aR^a$)$_n$O$R^a$;

$X^2$ is —N($R^a$)S(=O)$_2$(C$R^aR^a$)$_n$—, —N($R^a$)C(=O)(C$R^aR^a$)$_n$—, —O(C$R^aR^a$)$_n$—, —(C$R^aR^a$)$_n$O—, —(C$R^aR^a$)$_n$S(=O)$_m$—, —(C$R^aR^a$)$_n$N($R^a$)—, —N($R^a$)(C$R^aR^a$)$_n$—, —S(O)$_m$(C$R^aR^a$)$_n$—, —N($R^a$)(C$R^aR^a$)$_n$—, —S(=O)$_2$N($R^a$)(C$R^aR^a$)$_n$—, —N($R^a$)C(=O)O(C$R^aR^a$)$_n$—, —N($R^a$)C(=O)N$R^a$(C$R^aR^a$)$_n$—, —N($R^a$)C(=N$R^a$)N$R^a$(C$R^aR^a$)$_n$—, —OC(=O)N$R^a$(C$R^aR^a$)$_n$—, or —N($R^a$)S(=O)$_2$N$R^a$(C$R^aR^a$)$_n$—;

Z is hydrogen, —$C_{1-6}$alkyl, —$C_{2-6}$alkenyl, —$C_{2-6}$alkynyl, —C(=O)$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^aR^a$)$_n$Y, or —(C$R^aR^a$)$_n$O$R^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$ or —N$R^a C_{2-6}$alkylO$R^a$;

each $R^a$ is independently hydrogen or $R^b$;
each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$haloalkyl, —O$C_{1-4}$alkyl, —NH$_2$, —CN, —NH$C_{1-4}$alkyl, or —N($C_{1-4}$alkyl)$_2$;
each n is independently 0, 1, 2, or 3; and
each m is independently 0, 1, or 2.

In another embodiment of the compounds of Formula II, or the pharmaceutically acceptable salts thereof, either alone or in combination with any of the above or below embodiments, $R^1$ is hydrogen, halo, $C_{1-6}$alkyl, —O$C_{1-6}$alkyl, or —S$C_{1-6}$alkyl.

In another embodiment of the compounds of Formula II, or the pharmaceutically acceptable salts thereof, either alone or in combination with any of the above or below embodiments, $R^1$ is hydrogen, chlorine, methyl or —Omethyl.

In another embodiment of the compounds of Formula II, or the pharmaceutically acceptable salts thereof, either alone or in combination with any of the above or below embodiments, $X^2$ is —N($R^a$)S(=O)$_2$(C$R^a R^a$)$_n$—, —N($R^a$)S(=O)$_2$N$R^a$(C$R^a R^a$)$_n$—, or —O(C$R^a R^a$)$_n$—.

In another embodiment of the compounds of Formula II, or the pharmaceutically acceptable salts thereof, either alone or in combination with any of the above or below embodiments, $X^2$ is —NHS(=O)$_2$— or —O—.

In another embodiment of the compounds of Formula II, or the pharmaceutically acceptable salts thereof, either alone or in combination with any of the above or below embodiments, Z is —$C_{1-6}$alkyl or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$ or —N$R^a C_{2-6}$alkylO$R^a$.

In another embodiment of the compounds of Formula II, or the pharmaceutically acceptable salts thereof, either alone or in combination with any of the above or below embodiments, Z is methyl or phenyl substituted by 0, 1, 2 or 3 substituents independently selected from $C_{1-8}$alkyl, —$C_{2-6}$alkenyl, —$C_{2-6}$ alkynyl, $C_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$ or —N$R^a C_{2-6}$alkylO$R^a$.

In another embodiment of the compounds of Formula II, or the pharmaceutically acceptable salts thereof, either alone or in combination with any of the above or below embodiments, Z is methyl; or phenyl substituted with fluorine.

In another embodiment of the compounds of Formula II, or the pharmaceutically acceptable salts thereof, either alone or in combination with any of the above or below embodiments, $X^1$ is —CR.

In another embodiment of the compounds of Formula II, or the pharmaceutically acceptable salts thereof, either alone or in combination with any of the above or below embodiments, $X^1$ is —CH.

In another embodiment of the compounds of Formula II, or the pharmaceutically acceptable salts thereof, either alone or in combination with any of the above or below embodiments, $R^1$ is hydrogen, halo, $C_{1-6}$alkyl or —O$C_{1-6}$alkyl;
$X^2$ is —N($R^a$)S(=O)$_2$(C$R^a R^a$)$_n$—, —N($R^a$)S(=O)$_2$N$R^a$(C$R^a R^a$)$_n$—, or —O(C$R^a R^a$)$_n$—;
Z is —$C_{1-6}$alkyl or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$ or —N$R^a C_{2-6}$alkylO$R^a$; and
$X^1$ is —CR.

In another embodiment of the compounds of Formula II, or the pharmaceutically acceptable salts thereof, either alone or in combination with any of the above or below embodiments, $R^3$, $R^4$, and $R^5$ are independently hydrogen, halo or $C_{1-6}$alkyl.

In another embodiment of the compounds of Formula II, or the pharmaceutically acceptable salts thereof, either alone or in combination with any of the above or below embodiments, $R^3$ is hydrogen, halo or —$C_{1-6}$alkyl.

In another embodiment of the compounds of Formula II, or the pharmaceutically acceptable salts thereof, either alone or in combination with any of the above or below embodiments, $R^3$ is hydrogen.

In another embodiment of the compounds of Formula II, or the pharmaceutically acceptable salts thereof, either alone or in combination with any of the above or below embodiments, $X^2$ is —N($R^a$)S(=O)$_2$(C$R^a R^a$)$_n$— and Z is a saturated, partially saturated or unsaturated 5-, 6- or 7-membered monocyclic ring containing 0, 1, 2, 3 or 4 heteroatoms independently selected from N, O and S.

In another embodiment of the compounds of Formula II, or the pharmaceutically acceptable salts thereof, either alone or in combination with any of the above or below embodiments, $X^2$ is —NHS(=O)$_2$— and Z is selected from

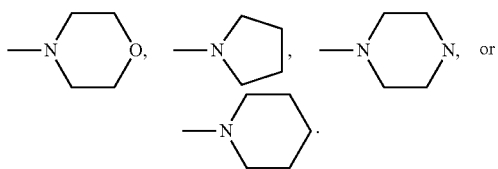

In a third embodiment, the present invention provides compounds of Formula III

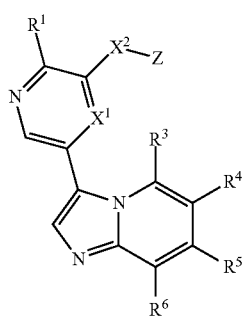

and the pharmaceutically acceptable salts thereof,
wherein $X^1$ is N or CR;

$R^1$ is hydrogen, halo, —$CF_3$, —$C_{1-6}$alkyl, —$C_{2-6}$alkenyl, —$C_{2-6}$alkynyl, —$OC_{1-6}$alkyl, —$SC_{1-6}$alkyl, or —CN, wherein the —$C_{1-6}$alkyl, —$C_{2-6}$alkenyl, or —$C_{2-6}$alkynyl are substituted by 0, 1, 2 or 3 substituents independently selected from —$C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, or a saturated, partially saturated or unsaturated 5-, 6- or 7-membered monocyclic ring or 6-, 7-, 8-, 9-, or 10-membered bicyclcic ring containing 0, 1, 2, 3 or 4 heteroatoms independently selected from N, O and S, wherein the ring is further substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each $R^3$, $R^4$, $R^5$ and $R^6$ are independently selected from hydrogen, $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—$C_{1-6}$alkylN($R^a$)C(=O)O$R^b$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)NR$^a$R$^a$, —N$R^aR^a$, —N($R^a$)C(=O)$R^b$, —N($R^a$)C(=O)O$R^b$, —N($R^a$)C(=O)N$R^aR^a$, —N($R^a$)C(=NR$^a$)NR$^a$R$^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, —$C_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, oxo, benzyl, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^aR^a$)$_n$Y, or —(C$R^aR^a$)$_n$O$R^a$;

$X^2$ is —N($R^a$)S(=O)$_2$(C$R^aR^a$)$_n$—, —N($R^a$)C(=O)(C$R^aR^a$)$_n$—, —O(C$R^aR^a$)$_n$—, —(C$R^aR^a$)$_n$)—, —(C$R^aR^a$)$_n$S(=O)$_m$—, —(C$R^aR^a$)$_n$N($R^a$)—, —N($R^a$)(C$R^aR^a$)$_n$—, —S(O)$_m$(C$R^aR^a$)$_n$—, —N($R^a$)(C$R^aR^a$)$_n$—, —S(=O)$_2$N($R^a$)(C$R^aR^a$)$_n$—, —N($R^a$)C(=O)O(C$R^aR^a$)$_n$—, —N($R^a$)C(=N$R^a$)N$R^a$(C$R^aR^a$)$_n$, —OC(=O)N$R^a$(C$R^aR^a$)$_n$—, or —N($R^a$)S(=O)$_2$N$R^a$(C$R^aR^a$)$_n$—;

Z is hydrogen, —$C_{1-6}$alkyl, —$C_{2-6}$alkenyl, —$C_{2-6}$alkynyl, —C(=O)$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, —$C_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)

$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —OC(=O)N($R^a$)S(=O)$_2R^b$, —OC$_{2-6}$alkyl$NR^aR^a$, —OC$_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2$$NR^aR^a$, —$NR^a$C$_{2-6}$alkyl$NR^aR^a$, —$NR^a$C$_{2-6}$alkyl$OR^a$, —N($R^a$)(CR$^a$R$^a$)$_n$—Y, —(CR$^a$R$^a$)$_n$Y, or —(CR$^a$R$^a$)$_n$$OR^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —OC(=O)N($R^a$)S(=O)$_2R^b$, —OC$_{2-6}$alkyl$NR^aR^a$, —OC$_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2$$NR^aR^a$, —$NR^a$C$_{2-6}$alkyl$NR^aR^a$ or —$NR^a$C$_{2-6}$alkyl$OR^a$;

each $R^a$ is independently hydrogen or $R^b$;

each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$halo alkyl, —OC$_{1-4}$alkyl, —NH$_2$, —CN, —NHC$_{1-4}$alkyl, or —N(C$_{1-4}$alkyl)$_2$;

each n is independently 0, 1, 2, or 3; and each m is independently 0, 1, or 2.

In another embodiment of the compounds of Formula III, or the pharmaceutically acceptable salts thereof, either alone or in combination with any of the above or below embodiments, $R^1$ is hydrogen, halo, $C_{1-6}$alkyl, —OC$_{1-6}$alkyl, or —SC$_{1-6}$alkyl.

In another embodiment of the compounds of Formula III, or the pharmaceutically acceptable salts thereof, either alone or in combination with any of the above or below embodiments, $R^1$ is hydrogen, chlorine, methyl or —Omethyl.

In another embodiment of the compounds of Formula III, or the pharmaceutically acceptable salts thereof, either alone or in combination with any of the above or below embodiments, $X^2$ is —N($R^a$)S(=O)$_2$(CR$^a$R$^a$)$_n$—, —N($R^a$)S(=O)$_2$$NR^a$(CR$^a$R$^a$)$_n$—, or —O(CR$^a$R$^a$)$_n$—.

In another embodiment of the compounds of Formula III, or the pharmaceutically acceptable salts thereof, either alone or in combination with any of the above or below embodiments, $X^2$ is —NHS(=O)$_2$— or —O—.

In another embodiment of the compounds of Formula III, or the pharmaceutically acceptable salts thereof, either alone or in combination with any of the above or below embodiments, Z is —$C_{1-6}$alkyl or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —OC(=O)N($R^a$)S(=O)$_2R^b$, —OC$_{2-6}$alkyl$NR^aR^a$, —OC$_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^a$C$_{2-6}$alkyl$NR^aR^a$ or —$NR^a$C$_{2-6}$alkyl$OR^a$.

In another embodiment of the compounds of Formula III, or the pharmaceutically acceptable salts thereof, either alone or in combination with any of the above or below embodiments, Z is methyl or phenyl substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —OC(=O)N($R^a$)S(=O)$_2R^b$, —OC$_{2-6}$alkyl$NR^aR^a$, —OC$_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^a$C$_{2-6}$alkyl$NR^aR^a$ or —$NR^a$C$_{2-6}$alkyl$OR^a$.

In another embodiment of the compounds of Formula III, or the pharmaceutically acceptable salts thereof, either alone or in combination with any of the above or below embodiments, Z is methyl; or phenyl substituted with fluorine.

In another embodiment of the compounds of Formula III, or the pharmaceutically acceptable salts thereof, either alone or in combination with any of the above or below embodiments, $X^1$ is —CR.

In another embodiment of the compounds of Formula III, or the pharmaceutically acceptable salts thereof, either alone or in combination with any of the above or below embodiments, $X^1$ is —CH.

In another embodiment of the compounds of Formula III, or the pharmaceutically acceptable salts thereof, either alone or in combination with any of the above or below embodiments, $R^1$ is hydrogen, halo, $C_{1-6}$alkyl, —OC$_{1-6}$alkyl, or —SC$_{1-6}$alkyl;

$X^2$ is —N($R^a$)S(=O)$_2$(CR$^a$R$^a$)$_n$—, —N($R^a$)S(=O)$_2NR^a$(CR$^a$R$^a$)$_n$—, or —O(CR$^a$R$^a$)$_n$—;

Z is —$C_{1-6}$alkyl or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —OC(=O)N($R^a$)S(=O)$_2R^b$, —OC$_{2-6}$alkyl$NR^aR^a$, —OC$_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^a$C$_{2-6}$alkyl$NR^aR^a$ or —$NR^a$C$_{2-6}$alkyl$OR^a$; and $X^1$ is —CR.

In another embodiment of the compounds of Formula III, or the pharmaceutically acceptable salts thereof, either alone or in combination with any of the above or below embodiments, $R^3$, $R^4$, $R^5$ and $R^6$ are independently hydrogen, halo, $C_{1-6}$alkyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, oxo, benzyl, cyano, nitro, —C(=O)$R^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, N(R$^a$)(CR$^a$R$^a$)$_n$—Y, —(CR$^a$R$^a$)$_n$Y, or —(CR$^a$R$^a$)$_n$OR$^a$.

In another embodiment of the compounds of Formula III, or the pharmaceutically acceptable salts thereof, either alone or in combination with any of the above or below embodiments, R$^4$ is hydrogen, C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$ alkyl, —C$_{2-6}$alkenyl, —C$_{2-6}$alkynyl, wherein the —C$_{1-6}$alkyl, —C$_{2-6}$alkenyl, —C$_{2-6}$alkynyl, are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, oxo, benzyl, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$.

In another embodiment of the compounds of Formula III, or the pharmaceutically acceptable salts thereof, either alone or in combination with any of the above or below embodiments, R$^4$ is hydrogen, halo, or C$_{1-6}$alkyl.

In another embodiment of the compounds of Formula III, or the pharmaceutically acceptable salts thereof, either alone or in combination with any of the above or below embodiments, R$^4$ is hydrogen.

In another embodiment of the compounds of Formula III, or the pharmaceutically acceptable salts thereof, either alone or in combination with any of the above or below embodiments, R$^3$, R$^4$, R$^5$ and R$^6$ are independently hydrogen, halo, C$_{1-6}$alkyl, pyridyl, morpholino, oxazolidinone, benzyl substituted oxazolidinone or benzyl.

In another embodiment of the compounds of Formula III, or the pharmaceutically acceptable salts thereof, either alone or in combination with any of the above or below embodiments, X$^2$ is —N(R$^a$)S(=O)$_2$(CR$^a$R$^a$)$_n$— and Z is a saturated, partially saturated or unsaturated 5-, 6- or 7-membered monocyclic ring containing 0, 1, 2, 3 or 4 heteroatoms independently selected from N, O and S.

In another embodiment of the compounds of Formula III, or the pharmaceutically acceptable salts thereof, either alone or in combination with any of the above or below embodiments, X$^2$ is —NHS(=O)$_2$— and Z is selected from

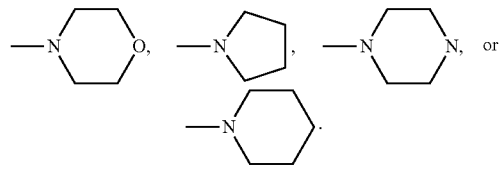

In a fourth embodiment, the present invention provides pharmaceutical compositions comprising: a compound of Formula I, II or III, or a pharmaceutically acceptable salt thereof; and a pharmaceutically acceptable excipient.

In another embodiment, the present invention provides the compounds, or the pharmaceutically acceptable salts thereof, selected from:
-(2-chloro-5-(2-methylimidazo[1,2-a]pyridin-3-yl)-3-pyridinyl)-4-fluorobenzenesulfonamide;
4-fluoro-N-(5-imidazo[1,2-a]pyridin-3-yl-3-pyridinyl)benzenesulfonamide;
N-(2-chloro-5-imidazo[1,2-a]pyridin-3-yl-3-pyridinyl)-4-fluorobenzenesulfonamide;
N-(2-chloro-5-(7-methylimidazo[1,2-a]pyridin-3-yl)-3-pyridinyl)-4-fluorobenzenesulfonamide;
N-(5-(6-bromo-2-methylimidazo[1,2-a]pyridin-3-yl)-2-chloro-3-pyridinyl)-4-fluorobenzenesulfonamide;
N-(5-(6-bromoimidazo[1,2-a]pyridin-3-yl)-2-chloro-3-pyridinyl)-4-fluorobenzenesulfonamide;
N-(2-chloro-5-(6-(4-pyridinyl)imidazo[1,2-a]pyridin-3-yl)-3-pyridinyl)-4-fluorobenzenesulfonamide;
N-(2-chloro-5-(6-(3-pyridinyl)imidazo[1,2-a]pyridin-3-yl)-3-pyridinyl)-4-fluorobenzenesulfonamide;
N-(2-chloro-5-(6-(4-morpholinyl)imidazo[1,2-a]pyridin-3-yl)-3-pyridinyl)-4-fluorobenzenesulfonamide;
3-(5,6-dimethoxy-3-pyridinyl)imidazo[1,2-a]pyridine;
6-bromo-3-(5,6-dimethoxy-3-pyridinyl)imidazo[1,2-a]pyridine;
3-(5,6-dimethoxy-3-pyridinyl)-6-(4-pyridinyl)imidazo[1,2-a]pyridine;
3-(3-(5,6-dimethoxy-3-pyridinyl)imidazo[1,2-a]pyridin-6-yl)-1,3-oxazolidin-2-one;
(4R)-4-benzyl-3-(3-(5,6-dimethoxy-3-pyridinyl)imidazo[1,2-a]pyridin-6-yl)-1,3-oxazolidin-2-one;
(4S)-4-benzyl-3-(3-(5,6-dimethoxy-3-pyridinyl)imidazo[1,2-a]pyridin-6-yl)-1,3-oxazolidin-2-one;
3-(5,6-dimethoxy-3-pyridinyl)-6-(4-morpholinyl)imidazo[1,2-a]pyridine;
N-(5-(6-benzyl-5-oxo-5,6-dihydroimidazo[1,2-c]pyrimidin-3-yl)-2-chloro-3-pyridinyl)-4-fluorobenzenesulfonamide;
N'-(2-chloro-5-(6-(4-pyridinyl)imidazo[1,2-a]pyridin-3-yl)-3-pyridinyl)-N,N-dimethylsulfamide;
N'-(2-chloro-5-(6-(2-(trifluoromethyl)-4-pyridinyl)imidazo[1,2-a]pyridin-3-yl)-3-pyridinyl)-N,N-dimethylsulfamide;
N-(2-chloro-5-(7-(3-pyridinyl)imidazo[1,2-a]pyridin-3-yl)-3-pyridinyl)methanesulfonamide;
N'-(2-chloro-5-(7-(4-pyridinyl)imidazo[1,2-a]pyridin-3-yl)-3-pyridinyl)-N,N-dimethylsulfamide;
N'-(2-chloro-5-(7-(3-pyridinyl)imidazo[1,2-a]pyridin-3-yl)-3-pyridinyl)-N,N-dimethylsulfamide;
N'-(2-chloro-5-(7-methyl-6-(4-pyridinyl)imidazo[1,2-a]pyridin-3-yl)-3-pyridinyl)-N,N-dimethylsulfamide;
N-(2-chloro-5-imidazo[1,2-a]pyrimidin-3-yl-3-pyridinyl)-4-fluorobenzenesulfonamide; or
N-(2-chloro-5-(6-chloroimidazo[1,2-b]pyridazin-3-yl)-3-pyridinyl)-4-fluorobenzenesulfonamide.

In a fifth embodiment, the present invention provides methods of treating melanoma, ovarian cancer, cervical cancer, breast cancer, colon cancer, rectal cancer, endometrial cancer, pancreatic cancer, lung cancer, stomach cancer, glioblastoma, liver cancer, prostate cancer, acute lyelogeous leukemia, chronic lyelogenous leukemia, or thyroid cancer, the methods comprising administering to a patient in need thereof a therapeutically effective amount of a compound of Formula I, II or III, or a pharmaceutically acceptable salt thereof.

DETAILED DESCRIPTION OF THE INVENTION

The present invention provides compounds of Formula I, II and III, as defined above, or the pharmaceutically acceptable salts thereof. The present invention also provides pharmaceutical compositions comprising a compound of Formula I, II or III, or a pharmaceutically acceptable salt thereof, and methods of treating diseases or conditions, such as cancer, using a compound of Formula I, II or III, or a pharmaceutically acceptable salt thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkly group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$ perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 3 heterotaoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b) pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b) pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)$ $OR^x$, —$C(=O)R^x$, wherein each $R^x$ is independently hydrogen or $C_1$-$C_8$alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, II or III, or a salt of a compound of Formula I, II or III, or a formulation containing a compound of Formula I, II or III, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$alkyl esters. Acceptable esters also include $C_5$-$C_7$ cycloalkyl esters, as well as arylalkyl esters such as benzyl. $C_1$-$C_4$alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic add functional group, a prodrug can comprise an ester formed by the replacement of the hydrogen atom of the add group with a group such as ($C_1$-$C_8$alkyl, ($C_2$-$Cl_2$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The compounds of the present invention are useful for the treatment of PI3K mediated diseases and disorders including melanomas, carcinomas, and other cancers. In one embodiment of the invention, there is provided a method of modulating a PI3K enzyme in a patient, the method comprising administering to a patient in need thereof a therapeutically effective amount of a compound of Formula I, II or III, or a pharmaceutically acceptable salt thereof. The present invention also concerns the use of a compound of Formula I, II or III, or a pharmaceutically acceptable salt thereof, for the manufacture of a medicament for the treatment of a PI3K mediated disease such as cancer.

The term "patient in need thereof" means a patient who has or is at risk of having a PI3K mediated disease or condition.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I, II or III, or a pharmaceutically acceptable salt thereof.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, chronic lyelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of the present invention can also be used to treat the following diseases or conditions: asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, athersoscleosis and Huntinton's disease.

The compounds of Formula I, II or III, or a pharmaceutically acceptable salt thereof, may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well know to those skilled in the art.

All patents and other publications recited herein are hereby incorporated by reference.

EXAMPLES

The examples presented below illustrate specific embodiments of the present invention. These examples are meant to be representative and are not intended to limit the scope of the claims in any manner. The starting materials for the specific examples below are generally available from commercial sources, unless otherwise specified. When helpful, commercial sources may be specifically indicated.

Analytical Methods:

Unless otherwise indicated, HPLC analyses were run on an Agilent Model 1100 system with an Agilent Technologies Zorbax SB-$C_8$ (5μ) reverse phase column (4.6×150 mm) run at 30° C. with a flow rate of about 1.50 mL/min (Agilent Technologies, Santa Clara, Calif.). The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Methods:

Unless otherwise indicated, samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% $HCO_2H$ or TFA) and solvent B (ACN/0.1% $HCO_2H$ or TFA) with a 5 to 9 min time period for a gradient from 10% to 90% solvent B. The gradient was followed by a 0.5 min period to return to 10% solvent B and a 2.5 min 10% solvent B re-equilibration (flush) of the column.

Preparative HPLC Methods:

Where indicated, compounds of the present invention were purified via reverse phase HPLC using a Gilson (Gilson, Middleton, Wis.) or Shimadzu (Columbia, Md.) workstation utilizing one of the following two protocols: (A) Using a 50×100 mm column (Waters, Exterra, C18, 5μ) (Waters, Milford, Mass.) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a ≥10 min gradient from 40% to 100% solvent B followed by a 5 min flow of 100% solvent B. The gradient was followed by a 2 min return to 40% solvent B; or (B) Using a Waters 20×50 mm column at 20 mL/min or Phenomenex Gemini 5μ C18 100×30 mm (Phenomenex, Torrance, Calif.). The mobile phase used was a mixture of solvent A ($H_2O$/0.1% TFA) and solvent B (ACN/0.1% TFA) with a ≥10 min gradient from 5% to 100% solvent B. The gradient is followed by a 2 min return to 5% ACN.

Proton NMR Spectra:

Unless otherwise indicated, all $^1$H NMR spectra were run on a Varian (Varian, Palo Alto, Calif.) series Mercury 300 MHz instrument or a Bruker (Bruker, Bilerica, Mass.) series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) or (M−H$^−$) molecular ion, depending on the ionization mode (positive or negative). The molecular ion reported was obtained by electrospray detection method. Compounds having an isotopic atom, such as bromine and the like, are reported according to the detected isotopic pattern, as appreciated by those skilled in the art.

The following abbreviations may be used herein:

| | |
|---|---|
| Ac$_2$O | acetic anhydride |
| ACN | acetonitrile |
| A-phos | Bis[(di-tert-butylphenyl phosphine)]palladium dichloride |
| aq | aqueous |
| ATP | adenosine 5'-triphosphate |
| Calcd or Calc'd | calculated |
| Conc. | concentrated |
| DCM | dichloromethane |
| DMAP | dimethyl aminopyridine |
| DME | dimethoxyl ethyl ether |
| DMF | N,N-dimethylformamide |
| DMSO | dimethyl sulfoxide |
| DTT | dithiothreitol |
| ESI | electrospray ionization |
| Et$_2$O | diethyl ether |
| Et$_3$N | triethylamine |
| EtOAc | ethyl acetate |
| EtOH | ethyl alcohol |
| FBS | fetal bovine serum |
| g | grams |
| h | hour |
| HCO$_2$H | formic acid |
| Hex | hexanes |
| HOAc | acetic acid |
| HPLC | high pressure liquid chromatography |
| IPA or iPrOH or iPr | isopropyl alcohol |
| iPr$_2$NEt | N-ethyl diisopropylamine |
| KOAc | potaisum hydroxyacetate |
| LCMS, LC-MS or LC/MS | liquid chromatography mass spectroscopy |
| m/z | mass divided by charge |
| MeCN | acetonitrile |
| MeI | iodomethane |
| MeOH | methyl alcohol |
| mg | milligrams |
| min | minutes |
| mL | milliliters |
| MS | mass spectra |
| MsCl | mesylchloride |
| NMP | 1-methyl-2-pyrrolidinone |
| NMR | nuclear magnetic resonance |
| PG | protecting group |
| PIP2 | phosphatidylinositol bisphosphate |
| Pos. ion | positive ion |
| py or pyr | pyridine |
| rt or RT | room temperature |
| Sat. | saturated |
| TFA | trifuoroacetic acid |
| TFAA | trifluoroacetic anhydride |
| THF | tetrahydrofuran |
| TMS | tetramethylsilane |
| Ts or tosyl | para-toluene sulfonyl |
| TsCl | para-toluene sulfonyl chloride |
| wt | Weight |

Percents of solid reagents specified are percent by weight with respect to the total weight, and percents of solvents are specified by percent by volume with respect to the total volume, unless indicated otherwise.

General Synthetic Schemes

Imidazo[1,2a]pyridine (I) can be prepared by the direct condensation (Scheme IA) between an 2-aminopyridine (C) and either an alpha-bromoacetophenone (A) under basic conditions (NaHCO$_3$ in DMF: *J. Am. Chem. Soc.,* 1954, 76, 4470-2) or an alpha-bromoketone (B) under neutral conditions (reflux in MeCN: *J. Chem. Crystallography,* 2000, 30, 109-113).

SCHEME IA

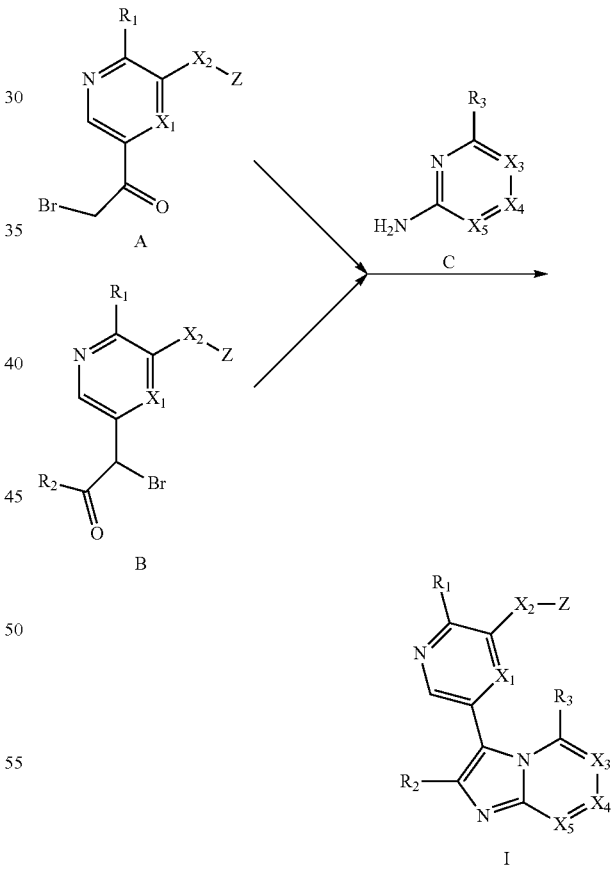

Alternatively, a suitably substituted imidazo[1,2a]pyridine (E) maybe coupled to a suitably substituted heteocycle (D) in the presence of a metal catalyst (Scheme IB). For example, regioselective palladium-catalyzed arylation and heteroarylation of imidazo[1,2a]pyridines (E, H=proton) maybe achieved (*Synlett,* 2006 (19), 3237-3242) with a bromide (D, B=Br). Halogenated imidazo[1,2a]pyridine (E, H=Cl, Br or I)

are readily synthesized under conventional halogenation conditions. These are readily coupled with a suitable boronic acid/ester (D, B=B(OH)$_2$ or B(OR)$_2$) under Suzuki reaction conditions (*J. Am. Chem. Soc.*, 2005, 127, 4685-4696).

SCHEME IB

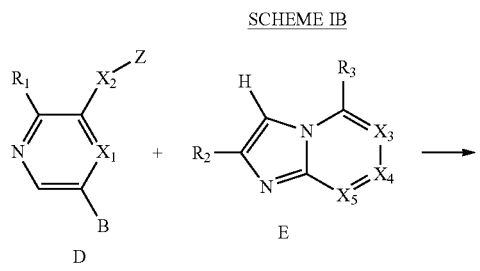

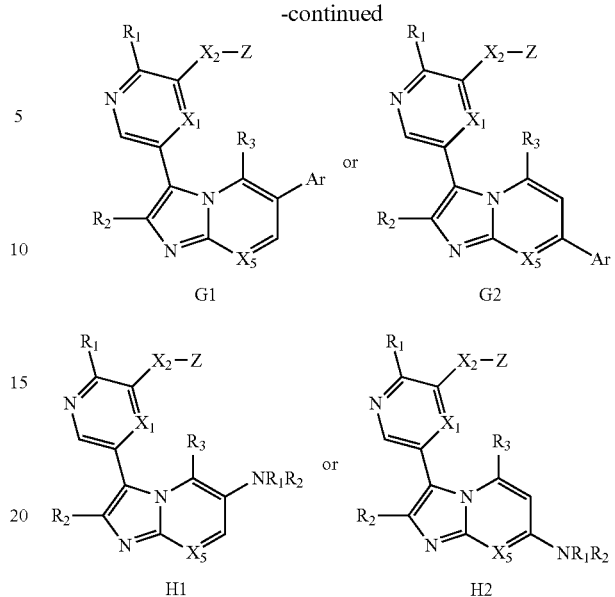

Another extension of Scheme IB applies to a suitably protected heterocycle D (X—Z: protected hetero atoms such as NBoc). The resulting intermediated J may be deprotected by conventional means to the parent K (Scheme ID). Functionalization of K may take the form of simple amide/ester formation, alkylation/reductive amination, or metal catalyzed coupling reactions. Particularly, treatment with a sulfonyl chloride leads to sulfonamides I (XZ=NHS(O$_2$)R).

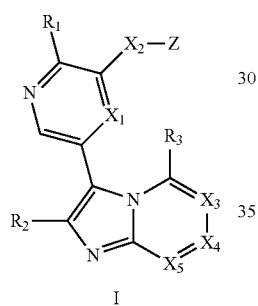

One extension of Scheme IB applies to imidazo[1,2a]pyridines where two halogens are differentiated such that region-selective coupling at the 3-position where H=I is possible in the presence of a bromine or chlorine at positions X3 or X4. The resulting intermediates (F1, F2) maybe further functionalized to G1/G2 under Suzuki conditions or to H1/H2 under metal catalyzed amination (*J. Org. Chem.* 2000, 65, 1144) or amidation (*J. Am. Chem. Soc.* 2002, 124, 7421) conditions (Scheme 1C).

SCHEME IC

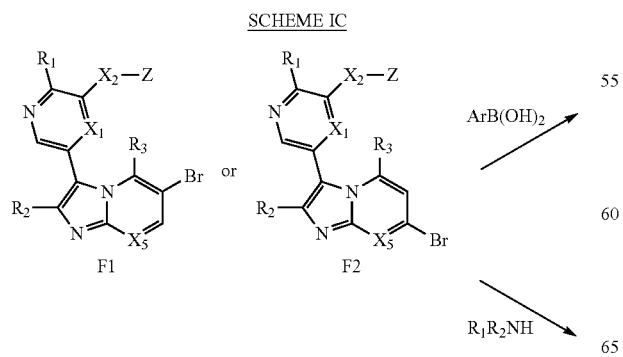

SCHEME ID

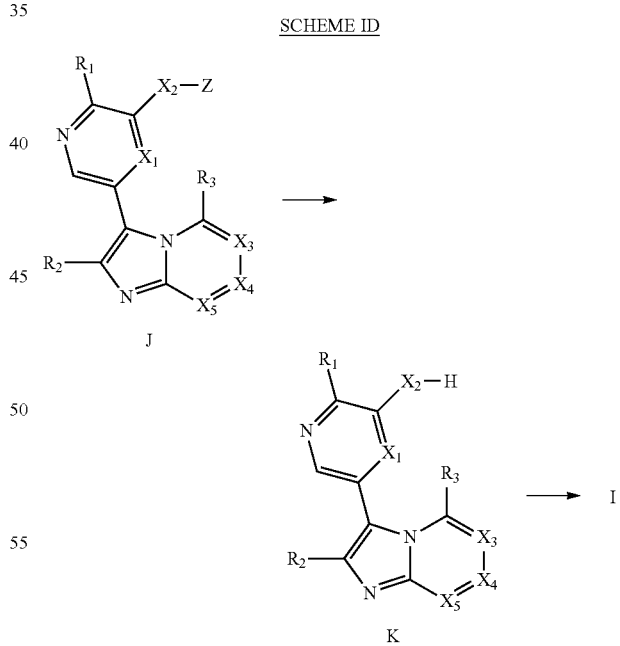

It maybe that in certain cases, pre-functionalization of the heterocycle D is advantageous. For example, amine L can be converted to a sulfonamide M (R=alkyl, aryl, or amino) in the presence of a suitable base. The presence of bromine in M allows either direct coupling with E or conversion to a boronic acid derivative N prior to the Suzuki coupling with yet another suitable halide E (Scheme IE).

SCHEME IE

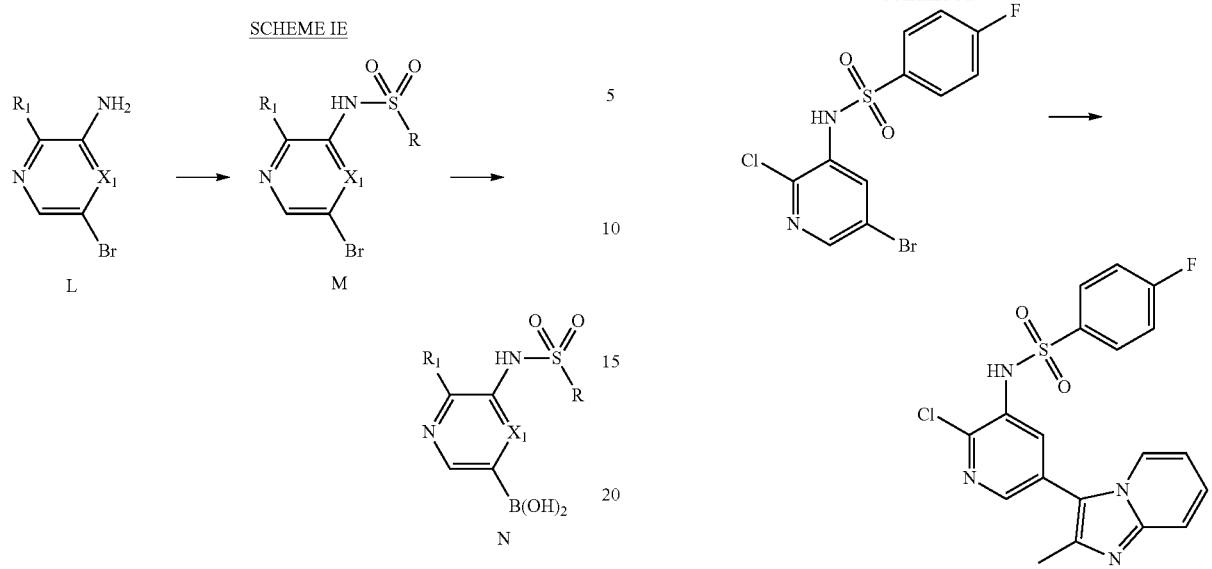

Example 1

N-(2-Chloro-5-(2-methylimidazo[1,2-a]pyridin-3-yl)-3-pyridinyl)-4-fluorobenzenesulfonamide

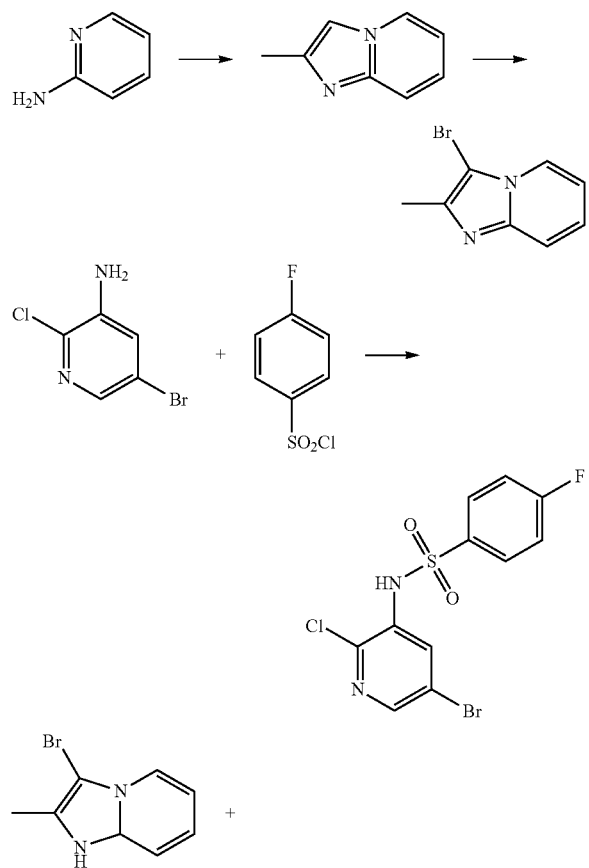

(1) 2-methylH-imidazo[1,2-a]pyridine. To a stirring solution of 2-aminopyridine (1.6 g, 17 mmol) in dimethylsulfoxide (9.6 mL, 136 mmol) was added chloroacetone (6.6 mL, 85 mmol). The reaction mixture was stirred at 23° C. for 1 hour. The resulting precipitate was then isolated by filtration and suspended in a hot $CHCl_3$/i-Pr (9:1; 20 mL). The suspension was cooled and the solid removed by filtration. The filtrate was then concentrated under reduced pressure and the product isolated as a white solid. MS (ESI positive ion) m/z: calcd exact mass for $C_8H_8N_2$: 132.1; found 133.2. $^1$H NMR (400 MHz, CHLOROFORM-d) δ ppm 2.64 (s, 3H) 7.24-7.36 (m, 1H) 7.63-7.81 (m, 1H) 7.90 (s, 1H) 8.14 (d, J=9.00 Hz, 1H) 8.73 (d, J=6.85 Hz, 1H).

(2) 3-bromo-2-methylH-imidazo[1,2-a]pyridine. To a stirring solution of 2-methylH-imidazo[1,2-a]pyridine (1.35 g, 10.2 mmol) in glacial acetic acid (5.8 mL, 102 mmol) was added bromine (0.52 ml, 10.2 mmol). After 5 min the solid was isolated by filtration then washed with both i-Pr (5 mL) and diethyl ether (5 mL). The solid was then partitioned between ethyl acetate (50 mL) and NaOH (pH=10). The organic layer was then dried over $MgSO_4$ and concentrated under reduced pressure to isolate product as light amber oil. MS (ESI positive ion) m/z: calcd exact mass for $C_8H_7BrN_2$: 210.0/212.0; found 211.0/213.0 (MH+). $^1$H NMR (400 MHz, CHLOROFORM-d) δ ppm 2.47 (s, 3H) 6.84-6.91 (m, 1H) 7.15-7.23 (m, 1H) 7.52 (d, J=9.00 Hz, 1H) 8.04 (d, J=6.85 Hz, 1H).

(3) N-(5-bromo-2-chloropyridin-3-yl)-4-fluorobenzenesulfonamide. A suspension of 5-bromo-2-chloropyridin-3-amine (10.0 g, 48 mmol), para-fluorobenzene sulfonyl chloride (20 g, 101 mmol), and pyridine (97 ml) was stirred at 23° C. for 24 hours. The solvent volume was then reduced by 50% under reduced pressure and the resulting solid collected by filtration. The solid, corresponding to N-(5-bromo-2-chloro pyridine-3-yl)-bis(4-fluoro)benzene sulfonamide, was then washed with i-Pr (2×25 mL) followed by diethyl ether (20 mL). A suspension of the above product (8.70 g, 17 mmol) and sodium methoxide, 25 wt. % in methanol (9 ml, 166 mmol) in MeOH (100 mL) were then stirred at 23° C. for 45 min. The reaction was then concentrated to a solid under reduced pressure followed by partitioning between $CHCl_3$ (80 mL) and 2M HCl (100 mL). The aqueous layer was then pH adjusted to 7 with 5% $NaHCO_3$. The organic phase was separated, dried over MgSO$_4$, and concentrated to a solid under reduced pressure. The solid was then suspended in hot ethyl acetate (20 mL), cooled, and isolated by filtration. MS (ESI positive) m/z calcd for C$_{11}$H$_7$BrClFN$_2$O$_2$S: 364.9/366.9; found 365.9/367.9 (M+1). $^1$H NMR (400 MHz, DMSO-d$_6$) δ ppm 7.37-7.50 (m, 2H) 7.77-7.86 (m, 2H) 7.94 (d, J=2.35 Hz, 1H) 8.43 (d, J=2.15 Hz, 1H) 10.64 (br. s., 1H).

(4) N-(2-chloro-5-(2-methylH-imidazo[1,2-a]pyridin-3-yl)pyridin-3-yl)-4-fluorobenzenesulfonamide. A suspension of N-(5-bromo-2-chloropyridin-3-yl)-4-fluorobenzenesulfonamide (1000 mg, 2735 µmol), bis(pinacolato)diboron (694.6 mg, 2735 mmol), dichloro[1,1'bis(diphenylphoshino)ferrocene]palladium(ii)dichloromethane adduct (200.1 mg, 273.5 µmol), potassium acetate (536.9 mg, 5470 µmol) in 1,4-dioxane (9 mL) was sparged with argon for 5 min then heated to 120° C. for 15 min. To the reaction was then added 3-bromo-2-methylH-imidazo[1,2-a]pyridine (577.3 mg, 2735 µmol), sodium carbonate (579.8 mg, 5470 µmol), and water (2 mL) then heated to 100° C. for 1 h. The reaction was then partitioned between 9:1 CHCl$_3$/i-Pr (50 mL) and 5% NaHCO$_3$ (15 mL). The aqueous layer then had the pH adjusted to 6 with 2M HCl. The organic was then dried over MgSO$_4$, concentrated, then purified on silica (80 g) eluting with 2 to 4% of 2M NH$_3$ in MeOH/CH$_2$Cl$_2$. Product was further purified on reverse phase HPLC eluting with water/ACN (0.1% TFA) on a Phenomenex C-18 10µ 30×150 mm column (Phenomenex, Torrance, Calif.). Desired fractions concentrated from toluene then dissolved in CH$_3$OH/CH$_2$Cl$_2$ (1:1; 5 mL) and stirred with Si-Carbonate (250 mg; 0.2 mmol) for 15 min. The filtrate was then isolated by filtration and concentrated to a white solid under reduced pressure. MS (ESI positive ion) m/z: calcd exact mass for C$_{19}$H$_{14}$ClFN$_4$O$_2$S: 416.0; found 417.0. $^1$H NMR (400 MHz, DMSO-d$_6$) δ ppm 2.33 (s, 3H) 6.91-6.98 (m, 1H) 7.31-7.39 (m, 1H) 7.40-7.48 (m, 2H) 7.60 (d, J=9.00 Hz, 1H) 7.78 (d, J=2.35 Hz, 1H) 7.80-7.91 (m, 2H) 8.23 (d, J=6.85 Hz, 1H) 8.41 (d, J=2.15 Hz, 1H) 10.89 (br. s., 1H)

Example 2

4-Fluoro-N-(5-imidazo[1,2-a]pyridin-3-yl-3-pyridinyl)benzenesulfonamide

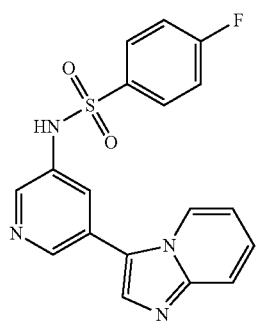 [SMILES: O=S(=O)(Nc1cncc(-c2cnc3ccccn23)c1)c1ccc(F)cc1]

(1) N-(5-bromopyridin-3-yl)-4-fluorobenzenesulfonamide A suspension of 3-amino-5-bromopyridine (2.50 g, 14.5 mmol), 4-fluorobenzenesulfonyl chloride (7.03 g, 36.1 mmol), pyridine (3.5 ml, 4.33 mmol), and i-Pr (10 mL) was appropriately sealed, stirred for 10 min at 23° C., then heated to 80° C. with microwaves for 10 min. Reaction was then partitioned between CH$_2$Cl$_2$ (75 mL) and 5% NaHCO$_3$ (25 mL). The separated organic was then dried over MgSO$_4$, concentrated, and purified on silica (80 g) eluting with 2 to 6% 2M NH$_3$ in CH$_3$OH/CH$_2$Cl$_2$. MS (ESI positive) m/z: calcd for C$_{11}$H$_8$BrFN$_2$O$_2$S: 330.0/332.0; found: 330.8/332.8 (M+1).

(2) N-(5-(H-imidazo[1,2-a]pyridin-3-yl)pyridin-3-yl)-4-fluorobenzenesulfonamide. A suspension of N-(5-bromopyridin-3-yl)-4-fluorobenzenesulfonamide (from Example 1) (200 mg, 604 µmol), bis(pinacolato)diboron (169 mg, 664 µmol), 1,1'-bis(diphenylphosphino)ferrocene-palladium(ii) dichloride dichloromethane complex (44.2 mg, 60.4 µmol), potassium acetate (119 mg, 1208 µmol) in 1,4-dioxane (2.5 mL) was sparged with argon for 5 min, appropriately sealed, then heated to 120° C. for 1 h. The reaction vessel was then charged with 3-bromoH-imidazo[1,2-a]pyridine (Alfa Aesar (USA), 149 mg, 755 µmol), sodium carbonate (192 mg; 1.82 mmol) and water (0.5 mL)-sparged with argon-then heated to 100° C. for 3 h. The reaction was then partitioned between 9:1 CHCl$_3$/i-Pr (25 mL) and 5% NaHCO$_3$ (10 mL). The remaining residue in the reaction vessel was dissolved in DMF (3 mL) and added to the separatory funnel. The aqueous layer was then adjusted to a pH of about 8 with 5M HCl, and aqueous further extracted with 9:1 CHCl$_3$/i-Pr (10 mL). The combined organics were dried over MgSO$_4$ then concentrated under reduced pressure. The product was purified on silica (24 g) eluting with 3 to 8% of 2M NH$_3$ in MeOH/CH$_2$Cl$_2$. Product then further purified on reverse phase HPLC eluting with water/acetonitrile (0.1% TFA). The desired fractions were then concentrated under reduced pressure, dissolved in CH$_3$OH/CH$_2$Cl$_2$ (1:1; 5 mL), and stirred with Si-Carbonate (250 mg; 0.2 mmol) for 15 min. The filtrate was isolated by filtration then concentrated to a white solid. MS (ESI positive) m/z: calcd exact mass for C$_{18}$H$_{13}$FN$_4$O$_2$S: 368.1; found 369.0. $^1$H NMR (400 MHz, DMSO-d$_6$) δ ppm 6.97-7.04 (m, 1H) 7.33-7.39 (m, 1H) 7.41-7.49 (m, 2H) 7.70 (d, J=9.00 Hz, 1H) 7.73 (t, J=2.15 Hz, 1H) 7.84 (s, 1H) 7.87-7.93 (m, 2H) 8.31 (d, J=2.35 Hz, 1H) 8.36 (d, J=6.85 Hz, 1H) 8.59 (d, J=1.76 Hz, 1H) 10.79 (br. s., 1H).

Example 3

N-(2-Chloro-5-imidazo[1,2-a]pyridin-3-yl-3-pyridinyl)-4-fluorobenzenesulfonamide

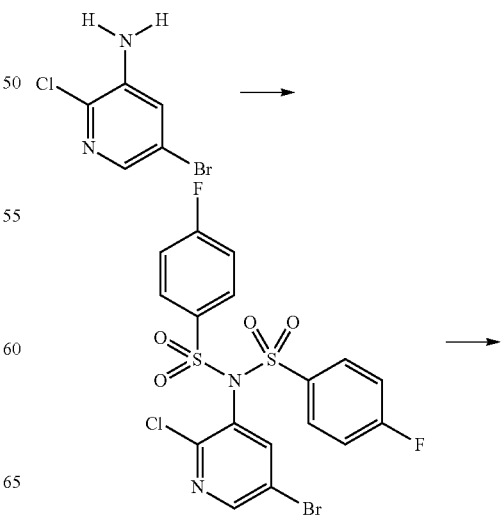

-continued

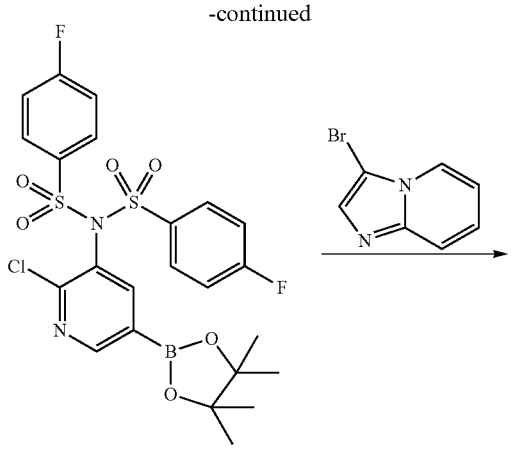

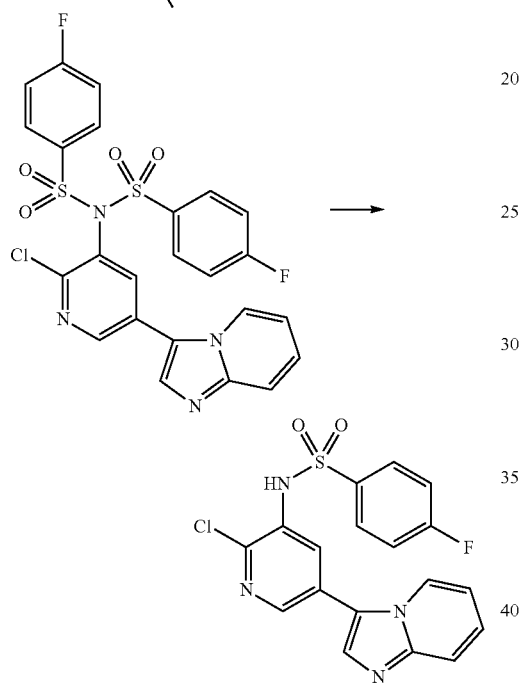

(1) N-(5-Boronic ester-2-chloro pyridine-3-yl)-bis(4-fluorobenzene sulfonamide). N-(5-bromo-2-chloro pyridine-3-yl)-bis(4-fluoro)benzene sulfonamide (2.0 g), 3.84 mmol), prepared from 5-bromo-2-chloropyridin-3-amine according to previously described procedure (Example 1, step 3), bis(pinacolato)diboron (0.97 g; 3.84 mmol), KOAc (1.0 g, 10.36 mmol), and Pd(dppf)Cl$_2$-CH$_2$Cl$_2$ (0.219 g; 0.2687 mmol) were taken in a sealed tube. To the contents of the sealed tube was added dry dioxane. The mixture was bubbled with N$_2$ for 30 min. The mixture was heated at 80° C. for 2 h. The mixture was quenched with water and extracted into ethyl acetate and concentrated to a solid (800 mg).

(2) N-(2-chloro-5-(H-imidazo[1,2-a]pyridin-3-yl)pyridin-3-yl)-bis(4-fluorobenzenesulfonamide). A mixture of N-(5-boronic ester-2-chloro pyridine-3-yl)-bis(4-fluorobenzene sulfonamide) (761 mg; 1.33 mmol), 3-bromoimidazo[1,2-a]pyridine (Paudler, W. W.; Blewitt, H. L. *J. Org. Chem.*, 1965, 30, 4081-4084) (200 mg, 1.02 mmol), Cs$_2$CO$_3$ (894 mg, 2.7 mmol), and Pd(PPh$_3$)$_4$ (59 mg, 0.052 mmol), in DME and H$_2$O was bubbled with nitrogen for about 1 h. The mixture was heated to 80° C. for 1 h and was cooled to rt. The mixture was quenched with water and extracted into the ethyl acetate layer. The organic layer was concentrated to give a solid (200 mg). MS (EI, pos.) calcd for C$_{24}$H$_{15}$ClF$_2$N$_4$O$_4$S$_2$: 560.0. found: 560.9 (M+1).

(3) N-(2-chloro-5-(H-imidazo[1,2-a]pyridin-3-yl)pyridin-3-yl)-4-fluorobenzenesulfonamide. A mixture of N-(2-chloro-5-(H-imidazo[1,2-a]pyridin-3-yl)pyridin-3-yl)-bis(4-fluorobenzenesulfonamide) (200 mg: 0.36 mmol) and K$_2$CO$_3$ (133 mg: 0.96 mm) in methanol was stirred for 6 h. The methanol was evaporated and the mixture was extracted into ethyl acetate layer and concentrate to give the desired product (150 mg). MS (EI, neg.) calcd for C$_{18}$H$_{12}$ClFN$_4$O$_2$S: 402.0; found: 400.9 (M−1). $^1$H NMR (400 MHz, DMSO-d$_6$) δ ppm 7.04 (t, J=6.46 Hz, 1H) 7.34-7.49 (m, 3H) 7.72 (d, J=9.00 Hz, 1H) 7.81-7.88 (m, 2H) 7.91 (s, 1H) 7.97 (d, J=2.15 Hz, 1H) 8.43 (d, J=7.04 Hz, 1H) 8.53 (d, J=2.15 Hz, 1H)

Example 4

N-(2-Chloro-5-(7-methylimidazo[1,2-a]pyridin-3-yl)-3-pyridinyl)-4-fluorobenzenesulfonamide

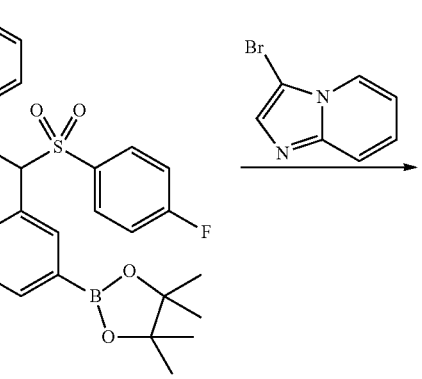

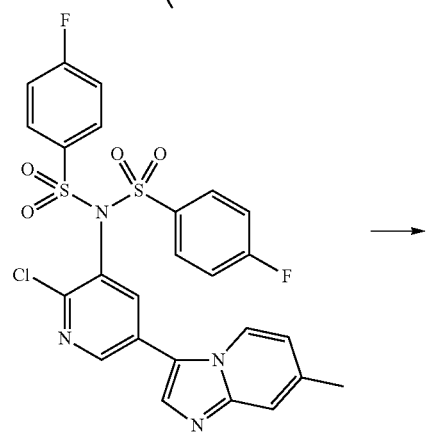

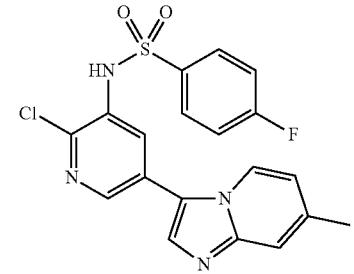

This compound was prepared in a similar manner as described in Example 3, using 3-bromo-7-methylH-imidazo[1,2-a]pyridine (WO 2001/038326) (15 mg, 0.71 mmol) and N-(5-boronic ester-2-chloro pyridine-3-yl)-bis(4-fluorobenzene sulfonamide) (530 mg, 0.93 mmol) to give, after basic hydrolysis, the final product (70 mg). MS (EI, pos.) calcd for $C_{19}H_{14}ClFN_4O_2S$: 416.0; found: 417.0 (M+1). $^1H$ NMR (300 MHz, DMSO-$d_6$) δ ppm 2.40 (s, 3H), 6.78 (dd, J=1.5, 5.4 Hz, 1H), 7.31 (t, J=6.0 Hz, 2H), 7.43 (s, 1H), 7.58 (m, 2H), 7.78 (m, 2H), 7.86 (bs, 1H), 7.90 (d, J=5.4 Hz, 1H).

Example 5

N-(5-(6-Bromo-2-methylimidazo[1,2-a]pyridin-3-yl)-2-chloro-3-pyridinyl)-4-fluorobenzenesulfonamide

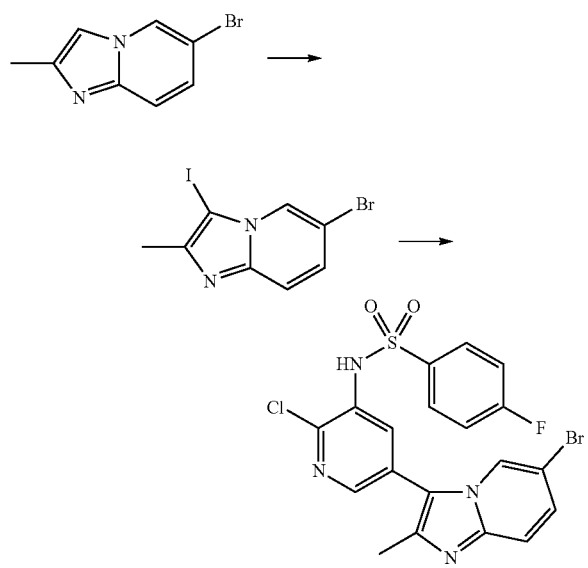

(1) 6-bromo-3-iodo-2-methylH-imidazo[1,2-a]pyridine. A cooled suspension of 6-bromo-2-methyl-imidazo[1,2-a]pyridine (Enguehard, C.; Hervet, M.; Thery, I.; Renou, J.-L.; Fauvelle, F.; Gueiffier, A. *Helv. Chimica Acta,* 2001, 84, 3610-3615) (2.5 g, 11.9 mmol) and sodium acetate (1.36 g, 16.7 mmol) in methanol (15 mL) was treated with Iodine (1.8 g, 14.3 mmol). After 3 h, the resulting solid was filtered and washed with water and dried. Triturating the solid with 5% ether/hexane furnished the product (1.5 g). MS (ES, pos.): calcd for $C_8H_6BrIN_2$: 335.9; found 336.7 (M+1). $^1H$ NMR (300 MHz, DMSO-$d_6$) δ ppm 2.40 (s, 3H), 7.40 (dd, 1H), 7.50 (d, 1H), 8.34 (s, 1H).

(2) N-(5-(6-bromo-2-methylH-imidazo[1,2-a]pyridin-3-yl)-2-chloropyridin-3-yl)-4-fluorobenzenesulfonamide. This compound was prepared in a similar manner as described in Example 3, using 6-bromo-3-iodo-2-methylH-imidazo[1,2-a]pyridine (1.5 g, 3.0 mmol) and N-(2-chloro-5-(H-imidazo[1,2-a]pyridin-3-yl)pyridin-3-yl)-bis(4-fluorobenzene-sulfonamide) (2.04 g, 3.58 mmol) to give, after hydrolysis, the product (0.70 g). LCMS (ES, pos.): calcd for $C_{19}H_{13}BrClFN_4O_2S$: 496.0; found: 497.0 (M+1). $^1H$ NMR (400 MHz, DMSO-$d_6$) δ ppm 2.23 (s, 3H) 7.31 (t, J=8.80 Hz, 2H) 7.37 (dd, J=9.49, 1.66 Hz, 1H) 7.52 (d, J=9.59 Hz, 1H) 7.56 (s, 1H) 7.80 (dd, J=8.61, 5.48 Hz, 2H) 7.96 (br. s., 1H) 8.26 (s, 1H) 10.62 (br. s., 1H)

Example 6

N-(5-(6-Bromoimidazo[1,2-a]pyridin-3-yl)-2-chloro-3-pyridinyl)-4-fluorobenzenesulfonamide

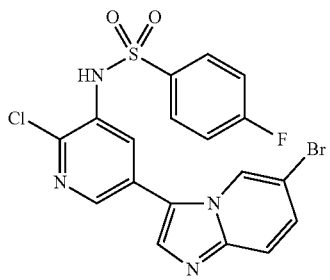 [SMILES: O=S(=O)(Nc1cc(-c2cnc3ccc(Br)cn23)cnc1Cl)c1ccc(F)cc1]

This compound was prepared in a similar manner as described in Example 3, using 6-bromo-3-iodoH-imidazo[1,2-a]pyridine (WO 2008014219) (1.0 g, 3.1 mmol) and N-(5-boronic ester-2-chloro pyridine-3-yl)-bis(4-fluorobenzene sulfonamide) (1.95 g, 3.42 mmol) to give, after hydrolysis, the product (0.88 g). LCMS (ES, pos.): calcd for $C_{18}H_{11}BrClFN_4O_2S$: 479.9; found: 480.9 (M+1). $^1H$ NMR (400 MHz, DMSO-$d_6$) δ ppm 7.36 (t, J=8.78 Hz, 2H) 7.47 (dd, J=9.54, 2.01 Hz, 1H) 7.68 (d, J=9.54 Hz, 1H) 7.77-7.86 (m, 3H) 7.88 (s, 1H) 8.25 (br. s., 1H) 8.55 (s, 1H) 10.62 (br. s., 1H)

Example 7

N-(2-Chloro-5-(6-(4-pyridinyl)imidazo[1,2-a]pyridin-3-yl)-3-pyridinyl)-4-fluorobenzenesulfonamide

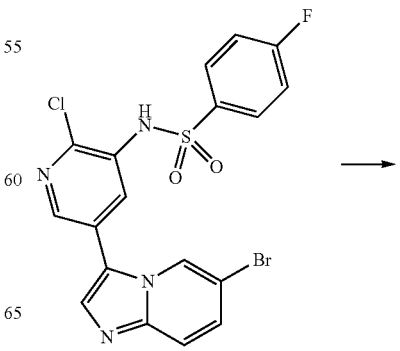

-continued

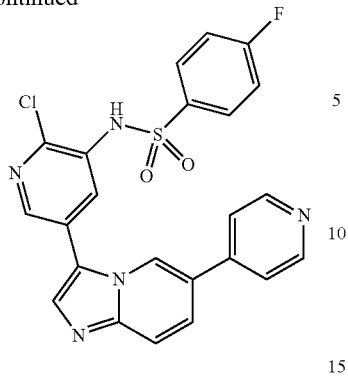

A mixture of N-(5-(6-bromoH-imidazo[1,2-a]pyridin-3-yl)-2-chloropyridin-3-yl)-4-fluorobenzenesulfonamide (200 mg, 0.42 mmol), pyridin-4-ylboronic acid (61 mg, 0.50 mmol), $Cs_2CO_3$ (365 mg, 1.12 mmol), and $Pd(PPh_3)_4$ (24 mg, 0.05 mmol), in DME-$H_2O$ was bubbled with nitrogen for about 1 h. The mixture was heated to 80° C. for 1 h and cooled to rt. Water was added the mixture was extracted with the ethyl acetate. The organic residue was purified on HPLC to yield the final product (70 mg). LCMS (ES, pos.): calcd for $C_{23}H_{15}ClFN_5O_2S$: 479.1; found: 480.1 (M+1). $^1$H NMR (400 MHz, DMSO-$d_6$) δ ppm 7.09 (t, J=8.78 Hz, 2H) 7.68-7.77 (m, 5H) 7.80 (d, J=5.52 Hz, 4H) 8.32 (s, 0H) 8.65 (d, J=6.02 Hz, 2H) 8.72 (s, 1H)

Example 8

N-(2-Chloro-5-(6-(3-pyridinyl)imidazo[1,2-a]pyridin-3-yl)-3-pyridinyl)-4-fluorobenzenesulfonamide

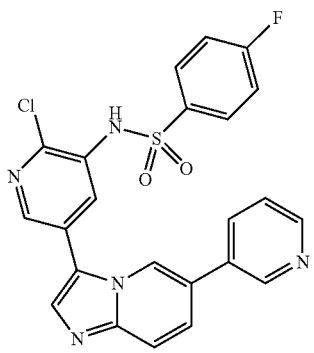 [SMILES: O=S(=O)(Nc1cc(-c2cnc3ccc(-c4cccnc4)cn23)cnc1Cl)c1ccc(F)cc1]

This compound was prepared (60 mg) in a similar manner as described in Example 7, using N-(5-(6-bromoH-imidazo[1,2-a]pyridin-3-yl)-2-chloropyridin-3-yl)-4-fluorobenzenesulfonamide (150 mg, 0.32 mmol) and pyridin-3-ylboronic acid (46 mg, 0.37 mmol). LCMS (ES, pos.): calcd for $C_{23}H_{15}ClFN_5O_2S$: 479.1; found: 480.1 (M+1). $^1$H NMR (400 MHz, DMSO-$d_6$) δ ppm 7.07 (t, J=8.78 Hz, 2H) 7.51 (dd, J=8.03, 5.02 Hz, 1H) 7.65-7.76 (m, 5H) 7.76-7.83 (m, 2H) 8.16 (d, J=8.03 Hz, 1H) 8.58-8.65 (m, 2H) 8.97 (d, J=2.01 Hz, 1H).

Example 9

N-(2-Chloro-5-(6-(4-morpholinyl)imidazo[1,2-a]pyridin-3-yl)-3-pyridinyl)-4-fluorobenzenesulfonamide

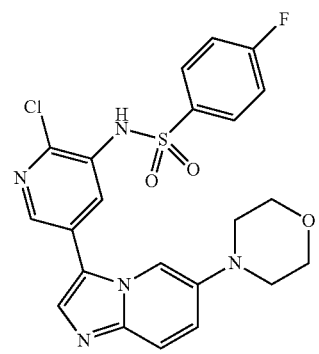 [SMILES: O=S(=O)(Nc1cc(-c2cnc3ccc(N4CCOCC4)cn23)cnc1Cl)c1ccc(F)cc1]

A mixture of N-(5-(6-bromoH-imidazo[1,2-a]pyridin-3-yl)-2-chloropyridin-3-yl)-4-fluorobenzenesulfonamide (400 mg, 0.83 mmol), $Pd_2(dba)_3$ (53 mg, 0.06 mmol), 4,5-bis(diphenylphosphino)-9,9-dimethylxanthene (Xantphos) (33 mg, 0.6 mmol), $Cs_2CO_3$ (730 mg, 2.25 mmol), and morpholine (4 mL) were stirred in a sealed tube at 80° C. for overnight. in a sealed tube to yield the product (30 mg). The reaction mixture was quenched with water and extracted into ethyl acetate. The organic layer was dried on $Na_2SO_4$ and concentrated. The crude material was purified on HPLC to yield the product (20 mg). LCMS (ES, pos.): calcd for $C_{22}H_{19}ClFN_5O_3S$: 487.0; found: 487.9 (M+1). $^1$H NMR (400 MHz, DMSO-$d_6$) δ ppm 3.10 (br. s., 4H) 3.75 (br. s., 4H) 7.43 (d, J=8.41 Hz, 3H) 7.61 (br. s., 1H) 7.83 (br. s., 4H) 8.12 (br. s., 1H) 8.51 (br. s., 1H) 10.79 (bs, 1H).

Example 10

3-(5,6-Dimethoxy-3-pyridinyl)imidazo[1,2-a]pyridine

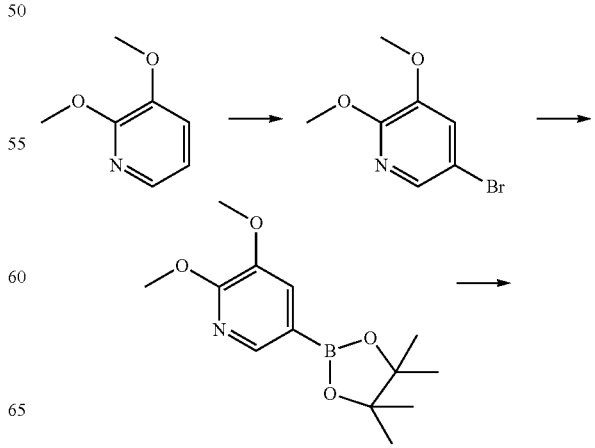

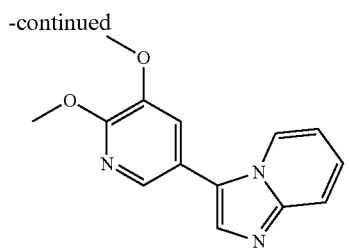

(1) 5-bromo-2,3-dimethoxypyridine. To a 100 mL round-bottomed flask was added 2,3-dimethoxypyridine (2 mL, 15 mmol), CH$_2$Cl$_2$ (30 mL), bromine (0.7 mL, 14 mmol). The reaction mixture was stirred at room temperature for overnight (ca 16 H). The reaction mixture was diluted with sat. NaHCO$_3$ (30 mL), and extracted with EtOAc (2×50 mL). The organic extract was washed with satd NaCl (20 mL), dried over Na$_2$SO$_4$, filtered and concentrated in vacuo and the residue was purified by silica gel chromatography, eluting with 50% CH$_2$Cl$_2$/hexanes to give 5-bromo-2,3-dimethoxypyridine (1.98 g, 60% yield). MS (ESI positive ion) m/z: calcd for C$_7$H$_8$BrNO$_2$: 217.0; found: 218.0 (M+1). $^1$H NMR (300 MHz, CHLOROFORM-d) δ ppm 3.87 (s, 3H) 3.99 (s, 3H) 7.14 (d, J=1.90 Hz, 1H) 7.78 (d, J=2.05 Hz, 1H).

(2) 2,3-dimethoxy-5-(4,4,5,5-tetramethyl-1,3,2-dioxaborolan-2-yl)pyridine. To a 100 mL round-bottomed flask was added 5-bromo-2,3-dimethoxypyridine (1.32 g, 6.05 mmol), dichloro 1,1'-bis(diphenylphosphino)ferrocene palladium (II) (0.494 g, 0.605 mmol), bis(pinacolato)diboron (2.31 g, 9.08 mmol), potassium acetate (1.51 ml, 24.2 mmol), dioxane (20 mL). The reaction mixture was stirred at 90° C. for 20 h. The mixture was cooed down to room temperature. The reaction mixture was diluted with water (40 mL) and extracted with EtOAc (2×40 mL). The organic extract was washed with satd NaCl (30 mL), dried over Na$_2$SO$_4$, filtered and concentrated in vacuo and the residue was purified by silica gel chromatograph, eluting with 30% EtOAc/hexanes. The solid was washed with hexanes to give 2,3-dimethoxy-5-(4,4,5,5-tetramethyl-1,3,2-dioxaborolan-2-yl)pyridine (1.21 g, 75.4% yield) as a white solid. MS (ESI positive ion) m/z: calcd for C$_{13}$H$_{20}$BNO$_4$: 265.1; found: 266.2 (M+1). $^1$H NMR (300 MHz, CHLOROFORM-d) δ ppm 1.34 (s, 12H) 3.90 (s, 3H) 4.04 (s, 3H) 7.34 (d, J=1.32 Hz, 1H) 8.13 (d, J=1.46 Hz, 1H).

(3) 3-(5,6-Dimethoxy-3-pyridinyl)imidazo[1,2-a]pyridine. To a 50 mL round-bottomed flask was added 3-bromoimidazo[1,2-a]pyridine (39 mg, 200 μmol), 2,3-dimethoxy-5-(4,4,5,5-tetramethyl-1,3,2-dioxaborolan-2-yl)pyridine (53 mg, 200 μmol), dichloro 1,1'-bis(diphenylphosphino)ferrocene palladium (II) (16 mg, 20 μmol), cesium carbonate (130 mg, 400 μmol), dioxane (1 mL), water (0.2 mL). The reaction mixture was stirred at 100° C. for 1 h. The mixture was cooled down to room temperature. The reaction mixture was diluted with satd NH$_4$Cl (5 mL) and extracted with EtOAc (2×20 mL). The organic extract was washed with satd NaCl (2 mL), dried over Na$_2$SO$_4$, filtered and concentrated in vacuo and the residue was purified by silica gel chromatography, eluting with 10% MeOH/EtOAc to give the final product (16 mg, 31% yield) as a white solid. MS (ESI positive ion) m/z: calcd for: C$_{14}$H$_{13}$N$_3$O$_2$ 255.1; found: 256.1 (M+1). $^1$H NMR (300 MHz, CHLOROFORM-d) δ ppm 3.93 (s, 3H) 4.10 (s, 3H) 6.80-6.87 (m, J=1.17 Hz, 1H) 7.17 (d, J=1.90 Hz, 1H) 7.18-7.25 (m, J=6.72, 1.17 Hz, 1H) 7.66-7.71 (m, J=1.02, 1.02 Hz, 2H) 7.94 (d, J=1.90 Hz, 1H) 8.19-8.25 (m, J=1.10, 1.10 Hz, 1H).

Example 11

6-Bromo-3-(5,6-dimethoxy-3-pyridinyl)imidazo[1,2-a]pyridine

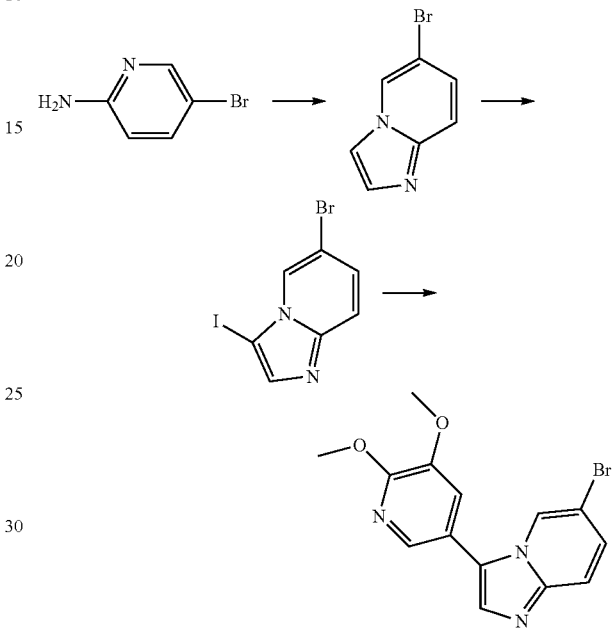

(1) 6-bromoimidazo[1,2-a]pyridine. To a 100 mL round-bottomed flask was added 2-amino-5-bromopyridine (5.04 g, 29.1 mmol), chloroacetaldehyde, approx. 50 wt. % solution in water (18.74 mL, 146 mmol), and EtOH (25 mL). The resulting reaction mixture was heated at 100° C. under N$_2$ for 4 h. The reaction was cooled to rt. Solvent was concentrated. The residue was redissolved in EtOAc. The organic layer was washed with sat. NaHCO$_3$ (2×40 mL), water (2×40 mL), brine, dried over MgSO$_4$ and removed solvent. The crude product was purified using SiO$_2$ chromatography (Teledyne Isco RediSep®, 120 g SiO$_2$, DCM:MeOH=96%:4% to DCM:MeOH (2M NH$_3$)=95%:5%, Flow=85 mL/min). Solvent was removed in vacuo to afford the desired product as brown solid (5.0 g). MS (ESI pos. ion) m/z: 196.9. Calcd exact mass for C$_7$H$_5$BrN$_2$: 195.9. $^1$H NMR (300 MHz, CHLOROFORM-d) δ ppm 7.24 (d, J=9.65 Hz, 1H) 7.54 (d, J=9.65 Hz, 1H) 7.57 (s, 1H) 7.65 (s, 1H) 8.30 (s, 1H).

(2) 6-bromo-3-iodoimidazo[1,2-a]pyridine. To a 150 mL round bottomed flask was added 6-bromoimidazo[1,2-a]pyridine (5.00 g, 25.4 mmol), anhydrous sodium acetate (5.69 g, 69.4 mmol) and MeOH (60 mL). The resulting mixture was cooled to 0° C. followed by adding iodine (7.13 g, 28.1 mmol). After the addition, ice bath was removed. It was warmed up to rt and continued to stir for 20 h. The precipitate in the reaction mixture was collected by filtration. The precipitate was washed with MeOH and dried to afford the desired product as light grey solid (7.0 g). MS (ESI pos. ion) m/z: 322.8. Calcd exact mass for C$_7$H$_4$BrIN$_2$: 321.9. $^1$H NMR (300 MHz, CHLOROFORM-d) δ ppm 7.30 (d, J=10.82 Hz, 1H) 7.52 (d, J=9.50 Hz, 1H) 7.71 (s, 1H) 8.29 (s, 1H).

(3) 6-Bromo-3-(5,6-dimethoxy-3-pyridinyl)imidazo[1,2-a]pyridine. To a 100 mL round bottomed flask was added 2,3-dimethoxy-5-(4,4,5,5-tetramethyl-1,3,2-dioxaborolan-2-yl)pyridine (0.80 g, 3.02 mmol, prepared from the corresponding bromide), 6-bromo-3-iodoimidazo[1,2-a]pyridine (1.17 g, 3.62 mmol), A-phos (Bis[(di-tert-butylphenyl phosphine)]palladium dichloride) (0.094 g, 0.15 mmol), potassium acetate (0.74 g, 7.54 mmol), water (1.5 mL), and 1-butanol (15 mL). The reaction was then heated at 100° C. under $N_2$ for 20 h. After cooled to rt, the 1-butanol was concentrated. The residue was partitioned between water/CHCl$_3$. The organic layer was dried over MgSO$_4$ and concentrated. The crude product was purified using SiO$_2$ chromatography (Teledyne Isco RediSep®, 12 g SiO$_2$ cartridge, methylene chloride/ethyl acetate/methanol=55%/43%/2%, Flow=30 mL/min). A peak at 18 min was collected. The solvent was removed in vacuo to afford the desired product as brown solid (450 mg). MS (ESI pos. ion) m/z: 333.9. Calcd exact mass for $C_{14}H_{12}BrN_3O_2$: 333.0. $^1$H NMR (300 MHz, CHLOROFORM-d) δ ppm 3.95 (s, 3H) 4.11 (s, 3H) 7.14 (s, 1H) 7.31 (d, J=9.50 Hz, 1H) 7.63 (d, J=9.50 Hz, 1H) 7.69 (s, 1H) 7.94 (s, 1H) 8.35 (s, 1H).

Example 12

3-(5,6-Dimethoxy-3-pyridinyl)-6-(4-pyridinyl)imidazo[1,2-a]pyridine

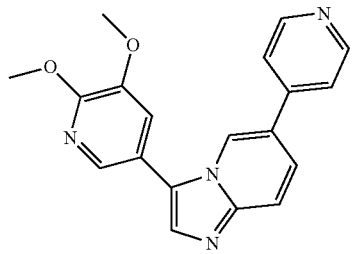 [SMILES: COc1cc(-c2cnc3ccc(-c4ccncc4)cn23)cnc1OC]

3-(5,6-dimethoxypyridin-3-yl)-6-(pyridin-4-yl)imidazo[1,2-a]pyridine. To a 5 mL microwave tube was added 6-bromo-3-(5,6-dimethoxypyridin-3-yl)H-imidazo[1,2-a]pyridine (0.070 g, 0.21 mmol), 4-pyridylboronic acid (0.031 g, 0.25 mmol), A-Phos, (Alfa Aesar, Ward Hill, Mass.) (0.0065 g, 0.010 mmol), potassium acetate (0.033 ml, 0.52 mmol), water (0.3 mL), and 1-butanol (3 mL). The reaction tube was then sealed and heated at 100° C. in closed system for 20 h. The mixture was concentrated. The residue was partitioned between water/chloroform. The organic layer was dried over MgSO$_4$ and concentrated. The crude product was purified using SiO$_2$ chromatography (Teledyne Isco RediSep®, 12 g SiO$_2$, methylene chloride:ethyl acetate:methanol=75%:23%:2%, Flow=30 mL/min). A peak at 22 min was collected. The solvent was removed in vacuo to afford the desired product as light brown solid. This crude product was re-purified using the reversed phase column (Varian, Solvent A: 0.1% TFA in water, Solvent B: 0.1% TFA in MeCN; method: 1-100% B/30 minutes). The product fraction was concentrated and the residue was dissolved in water and adjusted to a pH of about 7 using saturated NaHCO$_3$. The resulting mixture was extracted with CHCl$_3$. The organic layer was dried over MgSO$_4$ and concentrated to afford the desired product as off-white solid (15.0 mg). MS (ESI pos. ion) m/z: 333.01. Calcd exact mass for $C_{19}H_{16}N_4O_2$: 332.13. $^1$H NMR (300 MHz, CHLOROFORM-d) δ ppm 3.95 (s, 3H) 4.12 (s, 3H) 7.19 (s, 1H) 7.43-7.55 (m, 3H) 7.75 (s, 1H) 7.82 (d, J=9.21 Hz, 1H) 8.00 (s, 1H) 8.47 (s, 1H) 8.70 (d, J=5.12 Hz, 2H).

Example 13

3-(3-(5,6-Dimethoxy-3-pyridinyl)imidazo[1,2-a]pyridin-6-yl)-1,3-oxazolidin-2-one

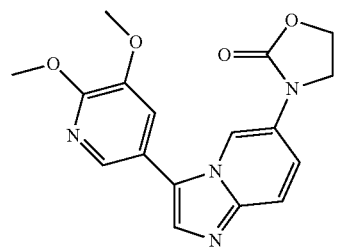 [SMILES: COc1cc(-c2cnc3ccc(N4CCOC4=O)cn23)cnc1OC]

To a 5 mL microwave tube was added 6-bromo-3-(5,6-dimethoxypyridin-3-yl)imidazo[1,2-a]pyridine (0.070 g, 0.21 mmol), 2-oxazolidinone (0.027 g, 0.31 mmol), copper(I) iodide (4.0 mg, 0.021 mmol), (1R,2R)—N1,N2-dimethylcyclohexane-1,2-diamine (0.0033 ml, 0.021 mmol), potassium carbonate (0.025 ml, 0.42 mmol), and dioxane (3 mL). The resulting reaction mixture was sealed and heated to 100° C. in closed system for 6 h. The mixture was cooled to rt and the solvent was removed. The crude product was purified using SiO$_2$ chromatography (Teledyne Isco RediSep®, 12 g SiO$_2$, methylene chloride:methanol=94%:6%, Flow=30 mL/min). A peak at 15 min was collected. The solvent was removed in vacuo to afford the desired product as white solid (20 mg). MS (ESI pos. ion) m/z: 341.0. Calcd exact mass for $C_{14}H_{12}BrN_3O_2$: 340.12. $^1$H NMR (300 MHz, DMSO-d$_6$) δ ppm 3.87 (s, 3H) 3.94 (s, 3H) 4.12 (t, J=7.89 Hz, 2H) 4.46 (t, J=7.89 Hz, 2H) 7.57 (s, 1H) 7.63 (d, J=1.61 Hz, 1H) 7.69-7.75 (m, 1H) 7.79 (s, 1H) 7.98 (s, 1H) 8.72 (s, 1H).

Example 14

(4R)-4-Benzyl-3-(3-(5,6-dimethoxy-3-pyridinyl)imidazo[1,2-a]pyridin-6-yl)-1,3-oxazolidin-2-one

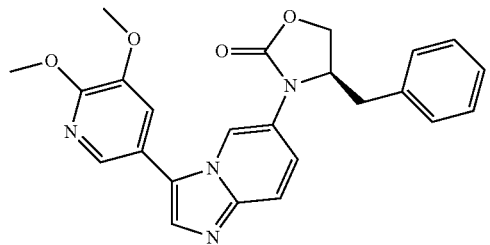 [SMILES: COc1cc(-c2cnc3ccc(N4C(=O)OC[C@H]4Cc4ccccc4)cn23)cnc1OC]

To a 5 mL microwave tube was added 6-bromo-3-(5,6-dimethoxypyridin-3-yl)H-imidazo[1,2-a]pyridine (0.070 g, 0.21 mmol), (R)-(+)-4-benzyl-2-oxazolidinone (0.056 g, 0.31 mmol), copper(I) iodide (0.0040 g, 0.021 mmol), (1R,2R)—N1,N2-dimethylcyclohexane-1,2-diamine (0.0033 ml, 0.021 mmol), potassium carbonate (0.058 g, 0.42 mmol), and dioxane (3 mL). The resulting reaction mixture was sealed and heated to 100° C. in closed system. After 6 h, the reaction was cooled to rt and concentrated. The residue was partitioned between water/chloroform. The organic layer was dried over MgSO$_4$ and concentrated. The crude product was purified on a reversed phase column (Phenomenex, Gemini 5 micron C18 100×30 mm) Solvent A: 0.1% TFA in water, Solvent B: 0.1% TFA in acetonitrile; 1-100% B over 30 min). The product fraction was concentrated and the residue was dissolved in water and adjusted to a pH of about 7 using saturated NaHCO$_3$ (ppt formed in the solution mixture). The resulting mixture was extracted with chloroform. The organic layer was dried over MgSO$_4$ and concentrated to an off-white solid. This was further purified in normal phase column using SiO$_2$ chromatography (Teledyne Isco RediSep®, 12 g SiO$_2$, DCM:MeOH=97%:3%, Flow=30 mL/min). The product fraction was concentrated in vacuo to afford the desired product as white solid (20.0 mg). The optical purity for this compound was 92% enantiomeric excess (ee) based on chiral HPLC analysis ((ADH 15×4.6 mm, 25% MeOH/DEA isocratic). MS (ESI pos. ion) m/z: 431.0. Calcd exact mass for C$_{24}$H$_{22}$N$_4$O$_4$: 430.2. $^1$H NMR (300 MHz, DMSO-d$_6$) δ ppm 2.80-2.95 (m, 1H) 2.97-3.07 (m, 1H) 3.87 (s, 3H) 3.96 (s, 3H) 4.20 (dd, J=8.70, 4.90 Hz, 1H) 4.41 (t, J=8.48 Hz, 1H) 4.82-4.97 (m, 1H) 7.10-7.27 (m, 5H) 7.51 (d, J=10.52 Hz, 1H) 7.57 (s, 1H) 7.71 (d, J=9.65 Hz, 1H) 7.81 (s, 1H) 7.98 (s, 1H) 8.74 (s, 1H).

Example 15

(4S)-4-Benzyl-3-(3-(5,6-dimethoxy-3-pyridinyl) imidazo[1,2-a]pyridin-6-yl)-1,3-oxazolidin-2-one

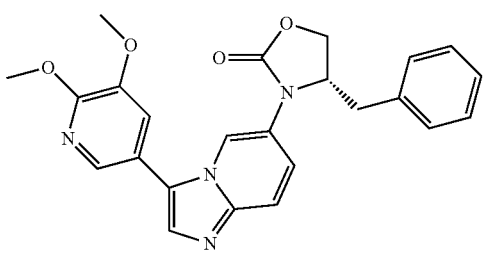 [SMILES: COc1cc(-c2cnc3ccc(N4C(=O)OC[C@@H]4Cc4ccccc4)cn23)cnc1OC]

This compound was prepared and purified as described for the (R)-isomer in Example 14, except (S)-(−)-4-benzyl-2-oxazolidinone was used, to give a white solid (23.0 mg). The optical purity for this compound was 100% ee based on chiral HPLC analysis (ADH 15×4.6 mm, 25% MeOH/DEA isocratic). MS (ESI pos. ion) m/z: 431.0. Calcd exact mass for C$_{24}$H$_{22}$N$_4$O$_4$: 430.16. $^1$H NMR (300 MHz, CHLOROFORM-d) δ ppm 2.80 (dd, J=13.59, 9.50 Hz, 1H) 3.13 (dd, J=13.67, 3.73 Hz, 1H) 3.97 (s, 3H) 4.12 (s, 3H) 4.27 (d, J=4.82 Hz, 1H) 4.43 (t, J=8.48 Hz, 1H) 4.54-4.68 (m, 1H) 7.11 (d, J=7.31 Hz, 2H) 7.21-7.35 (m, 5H) 7.70-7.79 (m, 2H) 7.97 (s, 1H) 8.67 (s, 1H).

Example 16

3-(5,6-Dimethoxy-3-pyridinyl)-6-(4-morpholinyl) imidazo[1,2-a]pyridine

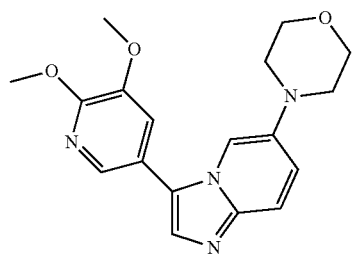 [SMILES: COc1cc(-c2cnc3ccc(N4CCOCC4)cn23)cnc1OC]

To a 5 mL microwave tube was added 6-bromo-3-(5,6-dimethoxypyridin-3-yl)imidazo[1,2-a]pyridine (0.050 g, 0.15 mmol), morpholine (0.020 g, 0.22 mmol), 2-(diphenylphosphino)-1-(2-(diphenylphosphino)naphthalen-1-yl) naphthalene (0.0028 g, 0.0045 mmol), Tris(dibenzylideneacetone)dipalladium(0) (0.0014 g, 0.0015 mmol), sodium tert-butoxide (0.020 g, 0.21 mmol), and toluene (3 mL). The resulting reaction mixture was sealed and heated to 100° C. in closed system for 6 h. The reaction was cooled and the solvent was removed. The crude product was purified using SiO$_2$ chromatography (Teledyne Isco RediSep®, 12 g SiO$_2$, DCM: MeOH=96%:4%, Flow=30 mL/min). The product fractions were collected. The solvent was removed in vacuo to afford the desired product as white solid (10.0 mg). MS (ESI pos. ion) m/z: 341.0. Calcd exact mass for C$_{18}$H$_{20}$N$_4$O$_3$: 340.2. $^1$H NMR (300 MHz, CHLOROFORM-d) δ ppm 2.99-3.09 (m, 4H) 3.84-3.92 (m, 4H) 3.94 (s, 3H) 4.11 (s, 3H) 7.12 (d, J=9.79 Hz, 1H) 7.17 (s, 1H) 7.57-7.65 (m, 3H) 7.96 (s, 1H).

Example 17

N-(5-(6-Benzyl-5-oxo-5,6-dihydroimidazo[1,2-c] pyrimidin-3-yl)-2-chloropyridin-3-yl)-4-fluorobenzenesulfonamide

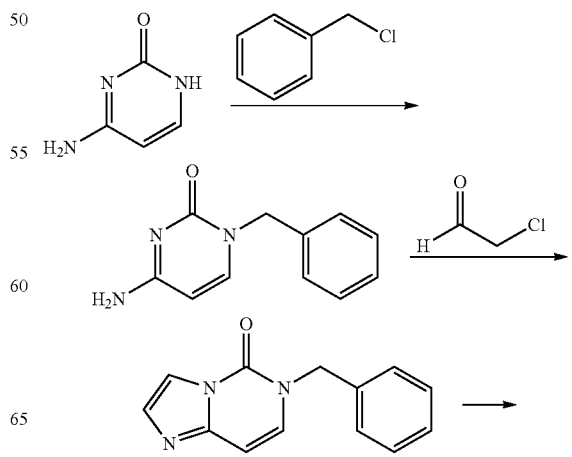

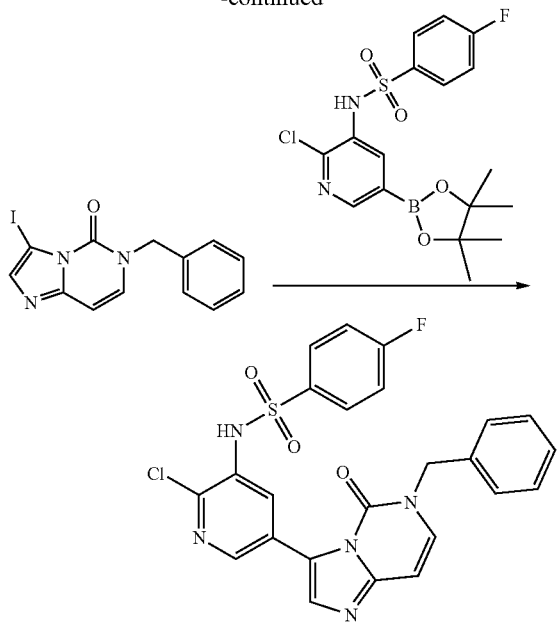

(1) 4-Amino-1-benzylpyrimidin-2(1H)-one. To a stirred mixture of cytosine (0.501 g, 4.50 mmol) and potassium carbonate (1.39 g, 9.97 mmol) in 10 mL of DMF in 20 mL microwave vial, benzyl chloride (0.519 mL, 4.50 mmol) was added and the mixture was stirred at room temperature for 3 days. The reaction mixture was diluted with water and white solid was collected via filtration, washed with water and air-dried to give the title compound as a white powder (0.748 g). m/z: calcd for $C_{11}H_{11}N_3O$: 201.1; found: 202.0 (M+1). $^1$H NMR (300 MHz, DMSO-$d_6$) δ ppm 4.85 (s, 2H) 5.67 (d, J=7.16 Hz, 1H) 7.03 (br. s., 2H) 7.20-7.38 (m, 5H) 7.67 (d, J=7.16 Hz, 1H).

(2) 6-Benzylimidazo[1,2-c]pyrimidin-5(6H)-one. To a 20 mL microwave vial, 4-amino-1-benzylpyrimidin-2(1H)-one (0.745 g, 3.70 mmol) and chloroacetaldehyde in water ((about 50% by wt, 2.40 mL, 18.65 mmol) were mixed into 5 mL of EtOH. The mixture was stirred at 100° C. for 4 h. After cooled to room temperature, the reaction mixture was concentrated in vacuo and the residue was taken into 30 mL of EtOAc. The organic phase was washed with saturated aqueous sodium bicarbonate (30 mL) and saturated aqueous sodium chloride (30 mL). The organic phase was dried over sodium sulfate, filtered and concentrated in vacuo. The crude product was purified by silica gel column chromatography (eluent: iPrOH in CHCl$_3$ 0-5%) to afford the title compound as brown solid (0.749 g). m/z: calc'd for $C_{13}H_{11}N_3O$: 225.1; found: 226.0 (M+1). $^1$H NMR (300 MHz, CHLOROFORM-d) δ ppm 5.14 (s, 2H) 6.61 (d, J=7.75 Hz, 1H) 7.01 (d, J=7.60 Hz, 1H) 7.29-7.45 (m, 6H) 7.77 (s, 1H).

(3) 6-Benzyl-3-iodoimidazo[1,2-c]pyrimidin-5(6H)-one. To a stirred solution of 6-benzylimidazo[1,2-c]pyrimidin-5(6H)-one (0.103 g, 0.455 mmol) and anhydrous sodium acetate (0.113 g, 1.38 mmol) in 3 mL of MeOH in a 5 mL microwave vial, iodine (0.252 g, 0.991 mmol) was added at 0° C. The brown solution was stirred at 0° C. for 30 min and then allowed to warm up to RT and stirred for 3 h. Additional iodine (0.304 g) was added at 0° C. and the mixture was stirred for overnight while warming up to RT. The solvent was evaporated and the residue was washed with water. The crude product was purified by silica gel column chromatography (eluent: EtOAc in hexanes 40%-100%) to afford the title compound (0.0734 g) as tan color solid. m/z: calcd for $C_{13}H_{10}IN_3O$: 351.0; found: 351.8 (M+1). $^1$H NMR (300 MHz, CHLOROFORM-d) δ ppm 6.57 (d, J=7.75 Hz, 1H) 6.98 (d, J=7.75 Hz, 1H) 7.29-7.47 (m, 6H).

(4) N-(5-(6-Benzyl-5-oxo-5,6-dihydroimidazo[1,2-c]pyrimidin-3-yl)-2-chloropyridin-3-yl)-4-fluorobenzenesulfonamide. To a 5 mL microwave reaction tube was added 6-benzyl-3-iodoimidazo[1,2-c]pyrimidin-5(6H)-one (0.0760 g, 0.216 mmol), N-(2-chloro-5-(4,4,5,5-tetramethyl-1,3,2-dioxaborolan-2-yl)pyridin-3-yl)-4-fluorobenzenesulfonamide (0.100 g, 0.242 mmol), PdCl$_2$(dppf)-DCM adduct (9.5 mg, 0.012 mmol) and potassium carbonate (0.271 mL, 0.541 mmol) in 1,4-dioxane (3 mL). The mixture was degassed by bubbling nitrogen through for 5 min. The tube was irradiated with microwave reactor at 80° C. for 10 min then again at 100° C. for 10 min. The reaction mixture was partitioned between Tris-HCl 1M pH7 (20 mL) and EtOAc (20 mL). The aqueous phase was extracted with EtOAc (20 mL). The combined organic phases were washed with saturated aqueous sodium chloride (30 mL). The organic phase was dried over sodium sulfate, filtered and concentrated in vacuo. The crude product was purified by silica gel column chromatography (eluent: iPrOH in CHCl$_3$ 0 to 5%) followed by a second chromatography (eluent: EtOAc in hexanes 50% to 100%) to afford the title compound as white solid (0.094 g). m/z: calcd for $C_{24}H_{17}ClFN_5O_3S$: 509.1; found: 509.8 (M+1). $^1$H NMR (300 MHz, CHLOROFORM-d) δ ppm 5.12 (s, 2H) 6.68 (d, J=7.75 Hz, 1H) 6.98 (s, 1H) 7.05-7.17 (m, 3H) 7.31-7.46 (m, 6H) 7.94 (d, J=5.12 Hz, 2H) 8.23 (d, J=15.35 Hz, 2H).

Intermediate Synthesis

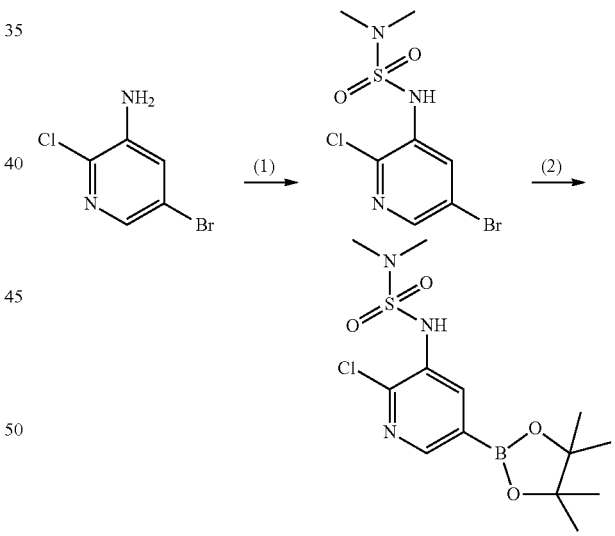

(1) N-(5-bromo-2-chloropyridine-3-yl)dimethylaminosulfonamide. To a solution of 5-bromo-2-chloropyridin-3-amine (10.00 g, 48.2 mmol) in pyridine (40.0 mL) was added dimethylamidosulfonyl chloride (31.1 mL, 289 mmol) and 4-dimethylaminopyridine (0.589 g, 4.82 mmol). The resulting mixture was heated to 100° C. under N$_2$ for 20 h. The reaction mixture was concentrated and the residue was partitioned between EtOAc and water. The aqueous layer was extracted with EtOAc (3×50 mL). The combined organic layers were washed with brine, dried over MgSO$_4$, and concentrated. The crude product was purified using SiO$_2$ chromatography (Teledyne Isco RediSep®, 330 g SiO$_2$, hexanes:

acetone=90%:10% to 80%:20%, Flow=100 mL/min) to afford the desired product as light brown solid (6.4 g). MS (ESI pos. ion) m/z: 313.8. Calcd exact mass for $C_7H_9BrClN_3O_2S$: 312.9. $^1$H NMR (300 MHz, CHLOROFORM-d) δ ppm 2.90 (s, 6H) 6.78 (br. s., 1H) 8.06 (s, 1H) 8.20 (s, 1H).

(2) N-(2-chloro-5-(4,4,5,5-tetramethyl-1,3,2-dioxaborolan-2-yl)pyridin-3-yl)dimethylaminosulfonamide. To a 250 mL round bottom flask was added N-(5-bromo-2-chloropyridine-3-yl)dimethylaminosulfonamide (3.00 g, 9.54 mmol), Bis(pinacolato)diboron (2.91 g, 11.44 mmol), 1,1'-bis(diphenylphosphino)ferrocene]dichloride palladium(II) (0.698 g, 0.954 mmol), potassium acetate (1.87 g, 19.07 mmol) and dioxane (60 mL). The resulting mixture was heated to 100° C. under $N_2$ for 20 h. The solvent was removed. The residue was partitioned between EtOAc and pH-7 buffer (1M TRIS-HCL). The aqueous layer was extracted with EtOAc (3×15 mL). The combined organic layers were dried over $MgSO_4$, and concentrated. The crude product was purified using $SiO_2$ chromatography (Teledyne Isco RediSep®, 40 g $SiO_2$, hexanes:EtOAc=80%:20%, Flow=40 mL/min) to afford the desired product as white solid (950 mg). MS (ESI pos. ion) m/z: 362.2. Calcd exact mass for $C_{13}H_{21}BClN_3O_4S$: 361.1. $^1$H NMR (300 MHz, CHLOROFORM-d) δ ppm 1.35 (s, 12H) 2.88 (s, 6H) 6.75 (br. s., 1H) 8.23 (s, 1H) 8.45 (s, 1H).

Example 18

N-(2-Chloro-5-(6-(pyridin-4-yl)imidazo[1,2-a]pyridin-3-yl)pyridin-3-yl)dimethylaminosulfonamide

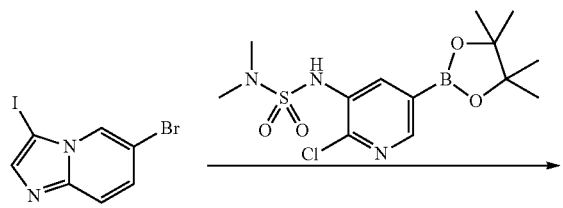

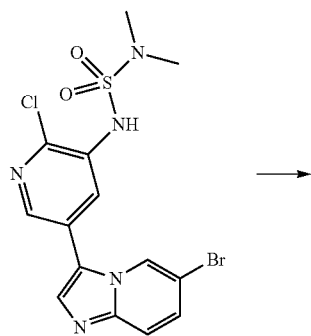

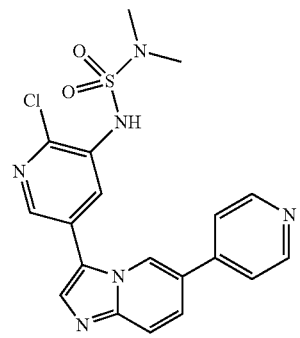

(1) N-(5-(6-bromoimidazo[1,2-a]pyridin-3-yl)-2-chloropyridin-3-yl)dimethylaminosulfonamide. To a 5 mL microwave tube was added N-(2-chloro-5-(4,4,5,5-tetramethyl-1,3,2-dioxaborolan-2-yl)pyridin-3-yl)dimethylaminosulfonamide (0.200 g, 0.553 mmol), 6-bromo-3-iodoimidazo[1,2-a]pyridine (0.214 g, 0.664 mmol), 1,1'-bis(diphenylphosphino)ferrocene]dichloride palladium(II) (0.020 g, 0.028 mmol), sodium carbonate (0.691 mL, 1.383 mmol), and dioxane (3 mL). The resulting mixture was sealed and underwent microwave heating at 110° C. for 15 min. The solvent was removed. The residue was partitioned between pH 7 buffer (1M TRIS-HCL) and DCM. The aqueous layer was extracted more with DCM (2×10 mL). The combined organic layers were dried over $MgSO_4$ and concentrated. The crude product was purified using $SiO_2$ chromatography (Teledyne Isco RediSep®, 12 g $SiO_2$, hexanes:acetone=80%:20%, Flow=30 mL/min). The solvent was removed in vacuo to afford the desired product as brown solid (180 mg). MS (ESI pos. ion) m/z: 429.7. Calcd exact mass for $C_{14}H_{13}BrClN_5O_2S$: 428.9. $^1$H NMR (300 MHz, CHLOROFORM-d) δ ppm 2.94 (s, 6H) 7.36 (d, J=9.65 Hz, 1H) 7.63 (d, J=9.50 Hz, 1H) 7.79 (s, 1H) 8.09 (s, 1H) 8.34 (s, 1H) 8.42 (s, 1H).

(2) N-(2-chloro-5-(6-(pyridin-4-yl)imidazo[1,2-a]pyridin-3-yl)pyridin-3-yl)dimethylaminosulfonamide. To a 5 mL microwave tube was added N-(5-(6-bromoimidazo[1,2-a]pyridin-3-yl)-2-chloropyridin-3-yl)dimethylaminosulfonamide (0.050 g, 0.116 mmol), pyridin-4-ylboronic acid (0.017 g, 0.139 mmol), 1,1'-bis(diphenylphosphino)ferrocene]dichloride palladium(II) (4.25 mg, 5.80 µmol), sodium carbonate (0.145 mL, 0.290 mmol), and dioxane (3 mL). The resulting mixture was sealed and underwent microwave heating at 100° C. for 20 min. The solvent was removed. The residue was partitioned between pH 7-buffer (1M TRIS-HCL) and DCM. The aqueous layer was extracted with DCM (3×10 mL). The combined organic layers were dried over $MgSO_4$ and concentrated. The crude product was purified using $SiO_2$ chromatography (Teledyne Isco RediSep®, 40 g $SiO_2$, DCM:MeOH (2M $NH_3$)=90%:10% Flow=40 mL/min) to afford the desired product as a light yellow solid (10.0 mg). MS (ESI pos. ion) m/z: 428.9. Calcd exact mass for $C_{19}H_{17}ClN_6O_2S$: 428.1. $^1$H NMR (300 MHz, CHLORO- FORM-d) δ ppm 2.89 (s, 6H) 6.95 (br. s., 1H) 7.50-7.65 (m, 3H) 7.82-7.93 (m, 2H) 8.23 (s, 1H) 8.40 (s, 1H) 8.64 (s, 1H) 8.74 (d, J=5.41 Hz, 2H).

Example 19

N-(2-Chloro-5-(6-(2-(trifluoromethyl)pyridin-4-yl) imidazo[1,2-a]pyridin-3-yl)pyridin-3-yl)dimethylaminosulfonamid

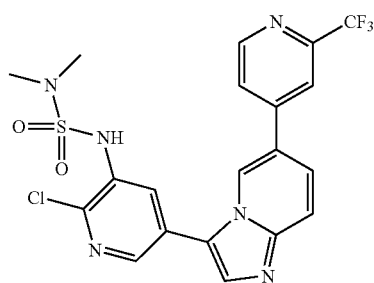 [SMILES: CN(C)S(=O)(=O)Nc1cc(-c2cnc3ccc(-c4ccnc(C(F)(F)F)c4)cn23)cnc1Cl]

To a 5 mL microwave tube was added N-(5-(6-bromoimidazo[1,2-a]pyridin-3-yl)-2-chloropyridin-3-yl)dimethylaminosulfonamide (0.080 g, 0.186 mmol), 4-(4,4,5,5-tetramethyl-1,3,2-dioxaborolan-2-yl)-2-(trifluoromethyl)pyridine (0.061 g, 0.223 mmol), 1,1'-bis(diphenylphosphino)ferrocene]dichloride palladium(II) (0.014 g, 0.019 mmol), sodium carbonate (0.232 mL, 0.464 mmol), and dioxane (2 mL). The resulting mixture was sealed and underwent microwave heating at 100° C. for 20 min. The solvent was removed. The residue was partitioned between pH 7-buffer (1M TRIS-HCL) and DCM. The aqueous layer was extracted with DCM (2×10 mL). The combined organic layers were dried over MgSO$_4$ and concentrated. The crude product was purified using SiO$_2$ chromatography (Teledyne Isco RediSep®, 40 g SiO$_2$, DCM:MeOH (2M NH$_3$)=90%:10% Flow=40 mL/min) to afford the desired product as light yellow solid (25.0 mg). MS (ESI pos. ion) m/z: 496.8. Calcd exact mass for C$_{20}$H$_{16}$ClF$_3$N$_6$O$_2$S: 496.1. $^1$H NMR (300 MHz, CHLOROFORM-d) δ ppm 2.92 (s, 6H) 6.93 (br. s., 1H) 7.78 (d, J=4.82 Hz, 1H) 7.91 (d, J=8.77 Hz, 1H) 7.96 (s, 1H) 8.07 (s, 1H) 8.22 (s, 1H) 8.33-8.44 (m, 2H) 8.70 (s, 1H) 8.90 (d, J=5.26 Hz, 1H).

Intermediate Synthesis 7-bromo-3-iodoimidazo[1,2-a]pyridine

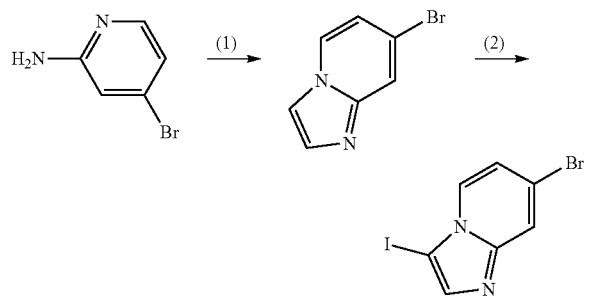

(1) 7-bromoimidazo[1,2-a]pyridine. To a 100 mL round-bottomed flask was added 4-bromopyridin-2-amine (4.0 g, 23.1 mmol), chloroacetaldehyde, 50% in water (14.9 mL, 116 mmol), and EtOH (25 mL). The resulting reaction mixture was heated at 100° C. under N$_2$ for 3 h. The reaction was cooled to rt and the solvent was concentrated. The residue was redissolved in EtOAc. The organic layer was washed with sat. NaHCO$_3$ (2×40 mL), water (2×40 mL), brine, dried over MgSO$_4$, and removed solvent. The crude product was purified using SiO$_2$ chromatography (Teledyne Isco RediSep®, 120 g SiO$_2$, DCM:MeOH=96%:4% to DCM:MeOH (2M NH$_3$)=95%:5%, Flow=85 mL/min). The solvent was removed in vacuo to afford the desired product as brown solid (3.8 g). MS (ESI pos. ion) m/z: 196.8. Calcd exact mass for C$_7$H$_5$BrN$_2$: 195.9. $^1$H NMR (300 MHz, CHLOROFORM-d) δ ppm 6.90 (d, J=7.16 Hz, 1H) 7.57 (s, 1H) 7.62 (s, 1H) 7.83 (s, 1H) 8.00 (d, J=7.16 Hz, 1H).

(2) 7-bromo-3-iodoimidazo[1,2-a]pyridine. To a 250 mL round bottomed flask was added 7-bromoimidazo[1,2-a]pyridine (3.8 g, 19.29 mmol), sodium acetate (4.3 g, 52.1 mmol) and MeOH (60 mL). The resulting mixture was cooled to 0° C. followed by adding diiodine (8.3 g, 32.8 mmol). After the addition, ice bath was removed and the mixture was continued to stir for 5 h. The solvent was concentrated. The crude product was purified using SiO$_2$ chromatography (Teledyne Isco RediSep®, 330 g SiO$_2$, hexanes:acetone=80%:20%, Flow=100 mL/min). The solvent was removed in vacuo to afford the desired product as light yellow solid (3.2 g). (ESI pos. ion) m/z: 322.8. Calcd exact mass for C$_7$H$_4$BrIN$_2$: 321.9. $^1$H NMR (300 MHz, CHLOROFORM-d) δ ppm 7.04 (d, J=7.02 Hz, 1H) 7.68 (s, 1H) 7.82 (s, 1H) 8.01 (d, J=7.31 Hz, 1H).

Example 20

N-(2-Chloro-5-(7-(pyridin-3-yl)imidazo[1,2-a]pyridin-3-yl)pyridin-3-yl)methanesulfonamide

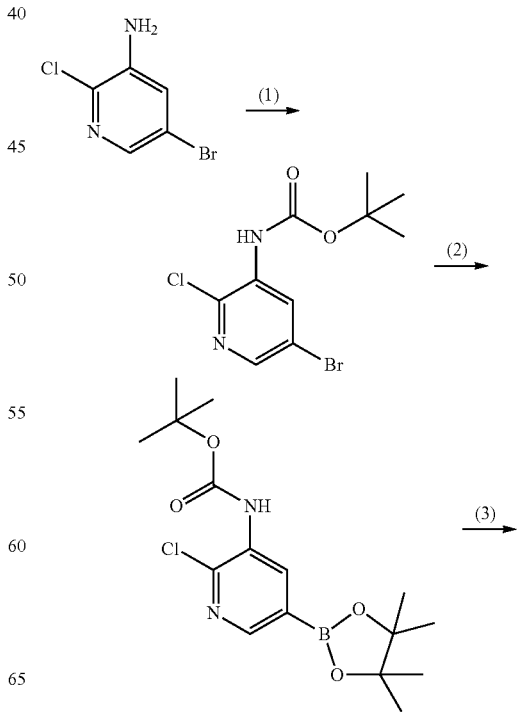

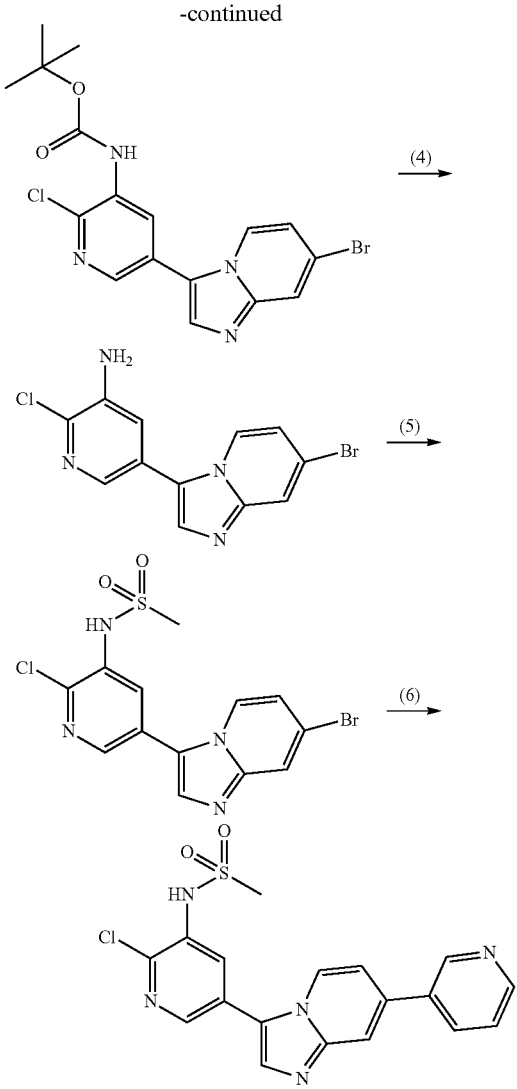

(1) tert-butyl 5-bromo-2-chloropyridin-3-ylcarbamate. To a solution of 5-bromo-2-chloropyridin-3-amine (2.000 g, 9.64 mmol) in THF (15 mL) cooled in an ice bath was added NaH (462 mg, 11.5 mmol, 60% dispersion in mineral oil). After stirring for 20 min, di-tert-butyl dicarbonate (2.52 g, 11.57 mmol) was added. The ice bath was removed and the reaction mixture was heated at 60° C. for 2 h. The mixture was cooled to rt and quenched with water. The solvent was removed. The residue was partitioned between EtOAc/water. The organic layer was washed with water, brine, dried over MgSO$_4$, and concentrated. The crude product was purified using SiO$_2$ chromatography (Teledyne Isco RediSep®, 120 g SiO$_2$, hexanes:acetone=80%:20%, Flow=85 mL/min). The solvent was removed in vacuo to afford the desired product as a white solid (1.6 g). MS (ESI pos. ion) m/z: 306.7. Calcd exact mass for C$_{10}$H$_{12}$BrClN$_2$O$_2$: 305.9. $^1$H NMR (300 MHz, CHLOROFORM-d) δ ppm 1.55 (s, 9H) 6.99 (br. s., 1H) 8.11 (s, 1H) 8.75 (s, 1H).

(2) tert-butyl 2-chloro-5-(4,4,5,5-tetramethyl-1,3,2-dioxaborolan-2-yl)pyridin-3-ylcarbamate. To a 20 mL microwave tube was added tert-butyl 5-bromo-2-chloropyridin-3-ylcarbamate (1.000 g, 3.25 mmol), bis(pinacolato)diboron (1.073 g, 4.23 mmol), 1,1′-bis(diphenylphosphino)ferrocene]dichloride palladium(II) (0.119 g, 0.163 mmol), potassium acetate (0.798 g, 8.13 mmol), and dioxane (8 mL). The resulting mixture was sealed and subject to microwave heating at 130° C. for 2×20 min. The solvent was removed. The residue was partitioned between water/CHCl$_3$. The aqueous layer was extracted with CHCl$_3$ (2×15 mL). The combined organic layers were dried over MgSO$_4$ and concentrated. The crude product was purified using SiO$_2$ chromatography (Teledyne Isco RediSep®, 80 g SiO$_2$, hexanes:EtOAc=80%:20%, Flow=60 mL/min) to afford the desired product as light yellow amorphous solid (110.0 mg). MS (ESI pos. ion) m/z: 272.9 (boronic acid). $^1$H NMR (300 MHz, CHLOROFORM-d) δ ppm 1.35 (s, 12H) 1.56 (s, 9H) 6.97 (br. s., 1H) 8.36 (s, 1H) 8.78 (s, 1H).

(3) tert-butyl 5-(7-bromoimidazo[1,2-a]pyridin-3-yl)-2-chloropyridin-3-ylcarbamate. To a 20 mL microwave tube was added tert-butyl 2-chloro-5-(4,4,5,5-tetramethyl-1,3,2-dioxaborolan-2-yl)pyridin-3-ylcarbamate (0.500 g, 1.410 mmol), 7-bromo-3-iodoimidazo[1,2-a]pyridine (0.501 g, 1.551 mmol), 1,1′-bis(diphenylphosphino)ferrocene]dichloride palladium(ii) (0.052 g, 0.070 mmol), sodium carbonate (1.762 mL, 3.52 mmol), and dioxane (15 mL). The resulting mixture was sealed and underwent microwave heating at 110° C. for 20 min. The solvent was removed. The residue was partitioned between water/CHCl$_3$. The organic layer was washed with water, brine, dried over MgSO$_4$ and concentrated. The crude product was purified using SiO$_2$ chromatography (Teledyne Isco RediSep®, 120 g SiO$_2$, DCM:EtOAc:MeOH=65%:32%:3%, Flow=85 mL/min) to afford the desired product as light yellow solid (380.0 mg). MS (ESI pos. ion) m/z: 423.2. Calcd exact mass for C$_{17}$H$_{16}$BrClN$_4$O$_2$: 422.1. $^1$H NMR (300 MHz, CHLOROFORM-d) δ ppm 1.56 (s, 9H) 7.03 (d, J=6.14 Hz, 1H) 7.12 (br. s., 1H) 7.77 (s, 1H) 7.90 (s, 1H) 8.14-8.28 (m, 2H) 8.76 (s, 1H).

(4) 5-(7-bromoimidazo[1,2-a]pyridin-3-yl)-2-chloropyridin-3-amine. To a solution of tert-butyl 5-(7-bromoimidazo[1,2-a]pyridin-3-yl)-2-chloropyridin-3-ylcarbamate (0.190 g, 0.448 mmol) in DCM (3 mL) in 20 mL scintillation vial was added 2,2,2-trifluoroacetic acid (2.59 mL, 33.6 mmol). After the addition, the vial was capped and the reaction mixture was stirred at rt for 3 h. The reaction mixture was adjusted to pH 7 using saturated NaHCO$_3$. The resulting mixture was extracted with DCM (3×10 mL). The combined organic layers were dried over MgSO$_4$ and concentrated. The crude product was purified using SiO$_2$ chromatography (Teledyne Isco RediSep®, 12 g SiO$_2$, DCM:MeOH (2M NH$_3$)=97%:3%, Flow=30 mL/min) to afford the desired product as light yellow solid (110 mg). MS (ESI pos. ion) m/z: 323.2. Calcd exact mass for C$_{12}$H$_8$BrClN$_4$: 322.1. $^1$H NMR (400 MHz, CHLOROFORM-d) δ ppm 4.29 (br. s., 2H) 6.97 (d, J=7.24 Hz, 1H) 7.16 (s, 1H) 7.69 (s, 1H) 7.89 (s, 1H) 7.99 (s, 1H) 8.12 (d, J=7.24 Hz, 1H).

(5) N-(5-(7-bromoimidazo[1,2-a]pyridin-3-yl)-2-chloropyridin-3-yl)methanesulfonamide. To a 5 mL microwave tube was added 5-(7-bromoimidazo[1,2-a]pyridin-3-yl)-2-chloropyridin-3-amine (0.100 g, 0.309 mmol), methanesulfonyl chloride (0.029 mL, 0.371 mmol), and pyridine (2 mL). The resulting mixture was sealed and heated at 100° C. for 3 h. The reaction mixture was cooled to rt and concentrated. The residue was partitioned between water and DCM. The aqueous layer was extracted with DCM (2×50 mL). The combined organic layers were dried over MgSO$_4$ and solvent removed. The crude product was purified using SiO$_2$ chromatography (Teledyne Isco RediSep®, 12 g SiO$_2$, DCM:EtOAc:MeOH (2M NH$_3$)=85%:12%:3%, Flow=30 mL/min) to afford the desired product as light brown solid (40.0 mg). MS (ESI pos. ion) m/z: 400.8. Calcd exact mass for C$_{13}$H$_{10}$BrClN$_4$O$_2$S: 399.9. $^1$H NMR (300 MHz, CHLORO- FORM-d) δ ppm 3.15 (s, 3H) 7.06 (d, J=7.02 Hz, 1H) 7.81 (s, 1H) 7.93 (s, 1H) 8.12-8.20 (m, 2H) 8.43 (s, 1H).

(6) N-(2-chloro-5-(7-(pyridin-3-yl)imidazo[1,2-a]pyridin-3-yl)pyridin-3-yl)methanesulfonamide. To a 5 mL microwave tube was added N-(5-(7-bromoimidazo[1,2-a]pyridin-3-yl)-2-chloropyridin-3-yl)methanesulfonamide (0.030 g, 0.075 mmol), 3-(4,4,5,5-tetramethyl-1,3,2-dioxaborolan-2-yl)pyridine (0.018 g, 0.090 mmol), 1,1'-bis(diphenylphosphino)ferrocene]dichloride palladium(II) (5.47 mg, 7.47 μmol), sodium carbonate (0.093 mL, 0.187 mmol), and dioxane (2 mL). The resulting mixture was sealed and underwent microwave heating at 100° C. for 20 min. The solvent was removed. The residue was partitioned between pH 7-buffer (1M TRIS-HCL) and DCM. The aqueous layer was extracted with DCM (3×50 mL). The combined organic layers were dried over MgSO$_4$ and concentrated. The crude product was purified on HPLC (Phenomenex, Gemni 5 micron C18 100×30 mm). The product residue was suspended in pH 7-buffer (1M TRIS-HCL) and was extracted with EtOAc (3×15 mL). The combined organic layers were dried over MgSO$_4$ and concentrated to afford the desired product as white solid (5.0 mg). MS (ESI pos. ion) m/z: 399.8. Calcd exact mass for $C_{18}H_{14}ClN_5O_2S$: 399.1. $^1$H NMR (300 MHz, MeOH) δ ppm 3.18 (s, 3H) 7.68-7.79 (m, 1H) 7.89 (d, J=7.02 Hz, 1H) 8.27-8.40 (m, 3H) 8.45 (d, J=8.18 Hz, 1H) 8.58 (s, 1H) 8.75 (br. s., 1H) 8.82 (d, J=7.31 Hz, 1H) 9.13 (br. s., 1H).

Example 21

N'-(2-Chloro-5-(7-(4-pyridinyl)imidazo[1,2-a]pyridin-3-yl)-3-pyridinyl)-N,N-dimethylsulfamide

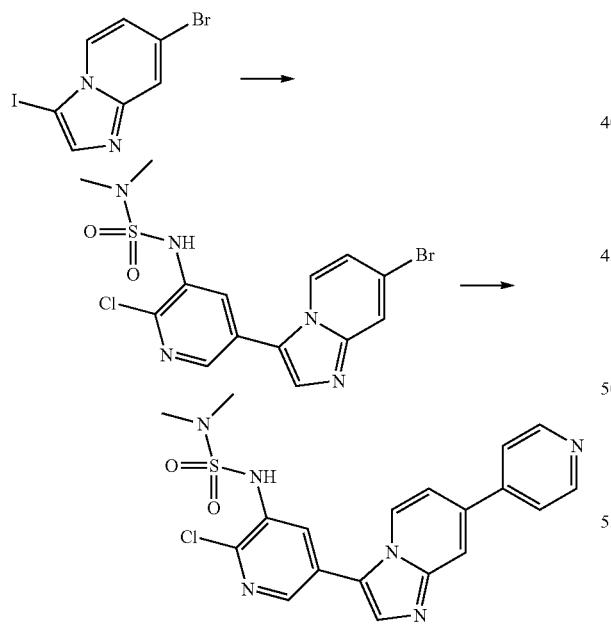

(1) N-(5-(7-bromoimidazo[1,2-a]pyridin-3-yl)-2-chloropyridin-3-yl)dimethylaminosulfonamide. To a 100 mL round bottom flask was added N-(5-bromo-2-chloropyridin-3-yl)dimethylaminosulfonamide (0.220 g, 0.699 mmol), Bis(pinacolato)diboron (0.266 g, 1.049 mmol), 1,1'-bis(diphenylphosphino)ferrocene]dichloride palladium(II) (0.051 g, 0.070 mmol), potassium acetate (0.069 g, 0.699 mmol) and dioxane (20 mL). The resulting mixture was heated at 95° C. under N$_2$ for 4 h. The reaction mixture was removed from the hot plate followed by the addition of 7-bromo-3-iodoimidazo[1,2-a]pyridine (0.226 g, 0.699 mmol), sodium carbonate (0.874 mL, 1.748 mmol), and 1,1'-bis(diphenylphosphino)ferrocene]dichloride palladium(II) (0.051 g, 0.070 mmol). The resulting mixture was then reheated at 95° C. under N$_2$ for 20 h. The reaction was cooled to rt. The solvent was removed. The residue was partitioned between pH 7-buffer (1M TRIS-HCL) and CHCl$_3$. The organic layer was dried over MgSO$_4$ and concentrated. The crude product was purified using SiO$_2$ chromatography (Teledyne Isco RediSep®, 40 g SiO$_2$, DCM:EtOAc:MeOH (2M NH$_3$)=80%:17%:3%, Flow=40 mL/min) to afford the desired product as brown foam-like solid (50.0 mg). MS (ESI pos. ion) m/z: 429.8. Calcd exact mass for $C_{14}H_{13}BrClN_5O_2S$: 428.9. $^1$H NMR (300 MHz, CHLOROFORM-d) δ ppm 2.91 (s, 6H) 6.88 (br. s., 1H) 7.04 (d, J=7.89 Hz, 1H) 7.78 (s, 1H) 7.93 (s, 1H) 8.08 (s, 1H) 8.16 (d, J=7.16 Hz, 1H) 8.34 (s, 1H).

(2) N'-(2-chloro-5-(7-(4-pyridinyl)imidazo[1,2-a]pyridin-3-yl)-3-pyridinyl)-N,N-dimethylsulfamide. To a 5 mL microwave tube was added N-(5-(7-bromoimidazo[1,2-a]pyridin-3-yl)-2-chloropyridin-3-yl)dimethylaminosulfonamide (0.050 g, 0.116 mmol), pyridin-4-ylboronic acid (0.017 g, 0.139 mmol), 1,1'-bis(diphenylphosphino)ferrocene]dichloride palladium(ii) (4.25 mg, 5.80 μmol), sodium carbonate (0.145 mL, 0.290 mmol), and dioxane (3 mL). The resulting mixture was sealed and underwent microwave heating at 100° C. for 20 min. The solvent was removed. The residue was partitioned between pH 7-buffer (1M TRIS-HCL) and DCM. The aqueous layer was extracted with DCM (2×10 mL). The combined organic layers were dried over MgSO$_4$ and concentrated. The crude product was purified using SiO$_2$ chromatography (Teledyne Isco RediSep®, 40 g SiO$_2$, DCM:MeOH (2M NH$_3$)=90%:10% Flow=40 mL/min) to afford the desired product as light yellow solid (5.0 mg). MS (ESI pos. ion) m/z: 428.9. Calcd exact mass for $C_{19}H_{17}ClN_6O_2S$: 428.1. $^1$H NMR (300 MHz, CHLOROFORM-d) δ ppm 2.93 (s, 6H) 6.92 (br. s., 1H) 7.24 (br. s., 1H) 7.60 (d, J=5.26 Hz, 2H) 7.90 (s, 1H) 8.05 (s, 1H) 8.16 (s, 1H) 8.37-8.48 (m, 2H) 8.76 (d, J=5.12 Hz, 2H).

Example 22

N'-(2-Chloro-5-(7-(3-pyridinyl)imidazo[1,2-a]pyridin-3-yl)-3-pyridinyl)-N,N-dimethylsulfamide

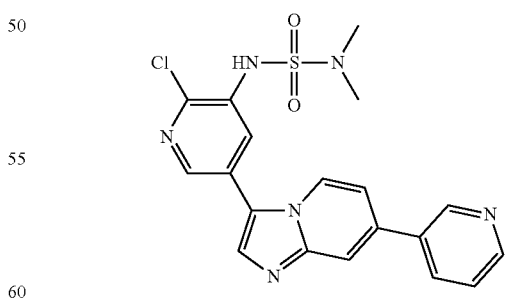

To a 5 mL microwave tube was added N-(5-(7-bromoimidazo[1,2-a]pyridin-3-yl)-2-chloropyridin-3-yl)dimethylaminosulfonamide (0.107 g, 0.248 mmol), 3-(4,4,5,5-tetramethyl-1,3,2-dioxaborolan-2-yl)pyridine (0.061 g, 0.298 mmol), 1,1'-bis(diphenylphosphino)ferrocene]dichloride palladium(II) (0.018 g, 0.025 mmol), sodium carbonate (0.311 mL, 0.621 mmol), and dioxane (3 mL). The resulting mixture was sealed and heated in a microwave at 110° C. for 20 min. Solvent was removed and the residue was partitioned between pH 7-buffer (1M TRIS-HCL) and DCM. The aqueous layer was extracted with DCM (2×15 mL). The combined organic layers were dried over MgSO$_4$ and concentrated. The crude material was purified using SiO$_2$ chromatography (Teledyne Isco RediSep®, P/N 68-2203-340, 40 g SiO$_2$, DCM:MeOH=97%:3% Flow=40 mL/min) to afford the desired product as light brown solid (55.0 mg). MS (EI, pos.) calcd for $C_{19}H_{17}ClN_6O_2S$: 428.1; found: 428.9.

$^1$H NMR (300 MHz, CHLOROFORM-d) δ ppm 2.93 (s, 6H) 6.92 (br. s., 1H) 7.23 (d, J=6.43 Hz, 1H) 7.41-7.52 (m, 1H) 7.88 (s, 1H) 7.92-8.03 (m, 2H) 8.16 (s, 1H) 8.36-8.47 (m, 2H) 8.69 (d, J=5.70 Hz, 1H) 8.97 (s, 1H).

Example 23

N'-(2-Chloro-5-(7-methyl-6-(4-pyridinyl)imidazo[1,2-a]pyridin-3-yl)-3-pyridinyl)-N,N-dimethylsulfamide

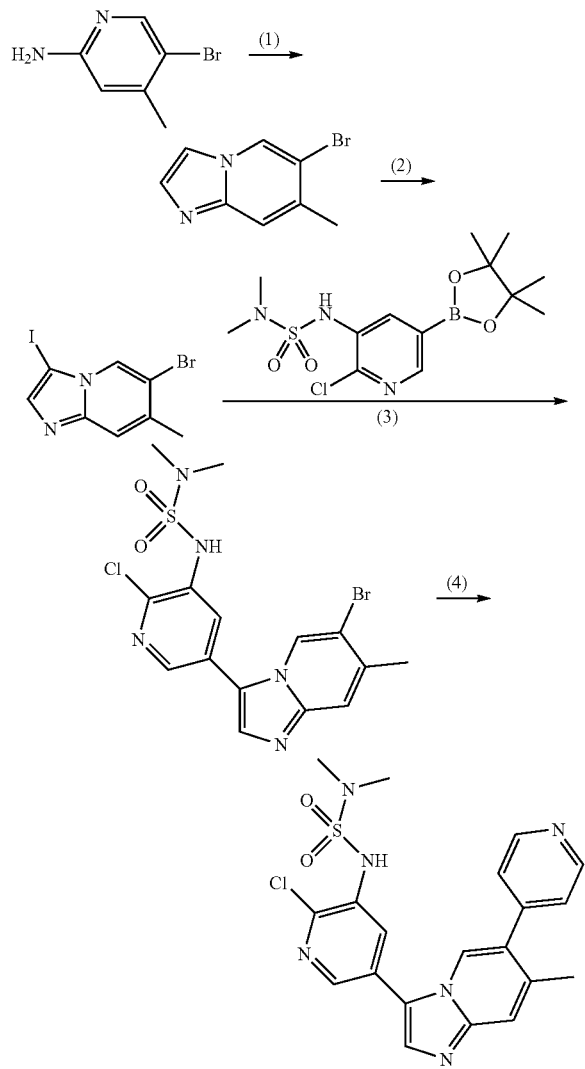

(1) 6-bromo-7-methylimidazo[1,2-a]pyridine. To a 100 mL round-bottomed flask was added 5-bromo-4-methylpyridin-2-amine (4.00 g, 21.39 mmol), chloroacetaldehyde (approx. 50 wt. % solution in water 13.76 mL, 107 mmol), and EtOH (25 mL). The resulting reaction mixture was heated at 100° C. under N$_2$ for 4 h. The solvent was removed. The residue was redissolved in EtOAc. The organic layer was washed with sat. NaHCO$_3$ (2×40 mL), water (2×40 mL), brine, dried over MgSO$_4$, and removed solvent. The crude product was purified using SiO$_2$ chromatography (Teledyne Isco RediSep®, 330 g SiO$_2$, hexanes:acetone=80%:20%, Flow=100 mL/min) to afford the desired product as a brown solid (4.3 g). MS (ESI pos. ion) m/z: 210.9. Calcd exact mass for $C_8H_7BrN_2$: 209.9. $^1$H NMR (300 MHz, CHLOROFORM-d) δ ppm 2.23 (s, 3H) 7.04 (s, 1H) 7.27 (s, 1H) 7.36 (s, 1H) 8.10 (s, 1H).

(2) 6-bromo-3-iodo-7-methylimidazo[1,2-a]pyridine. To a 150 mL round bottomed flask was added 6-bromo-7-methylimidazo[1,2-a]pyridine (4.300 g, 20.37 mmol), sodium acetate anhydrous (2.95 mL, 55.0 mmol) and MeOH (60 mL). The resulting mixture was cooled to 0° C. followed by adding iodine (5.7 g, 22.41 mmol). After the addition, ice bath was removed. After 20 h, the solid in the reaction mixture was collected by filtration. The solid was washed with MeOH affording the desired product as a light grey solid (5.1 g). MS (ESI pos. ion) m/z: 336.7. Calcd exact mass for $C_8H_6BrIN_2$: 335.9. $^1$H NMR (300 MHz, CHLOROFORM-d) δ ppm 2.50 (s, 3H) 7.49 (s, 1H) 7.64 (s, 1H) 8.30 (s, 1H).

(3) N-(5-(6-bromo-7-methylimidazo[1,2-a]pyridin-3-yl)-2-chloropyridin-3-yl)dimethylaminosulfonamide. To a 5 mL microwave tube was added N-(2-chloro-5-(4,4,5,5,-tetramethyl-1,3,2-dioxaborolan-2-yl)pyridine-3-yl)-N',N'-dimethylsulfonamide (0.300 g, 0.830 mmol), 6-bromo-3-iodo-7-methylimidazo[1,2-a]pyridine (0.335 g, 0.995 mmol), 1,1'-bis(diphenylphosphino)ferrocene]dichloride palladium(ii) (0.061 g, 0.083 mmol), sodium carbonate (1.037 mL, 2.074 mmol), and dioxane (3 mL). The resulting mixture was sealed and underwent microwave heating at 110° C. for 20 min. The solvent was removed. The residue was partitioned between pH 7-buffer (1M TRIS-HCL) and DCM. The aqueous layer was extracted more with DCM (2×10 mL). The combined organic layer was dried over MgSO$_4$ and concentrated. The crude product was purified using SiO$_2$ chromatography (Teledyne Isco RediSep®, 80 g SiO$_2$, DCM:EtOAc:MeOH=65%:32%:3%, Flow=65 mL/min). The solvent was removed in vacuo to afford the desired product as light yellow solid (160 mg). MS (ESI pos. ion) m/z: 443.8. Calcd exact mass for $C_{15}H_{15}BrClN_5O_2S$: 442.9. $^1$H NMR (300 MHz, CHLOROFORM-d) δ ppm 2.51 (s, 3H) 2.95 (s, 6H) 6.92 (br. s., 1H) 7.59 (s, 1H) 7.75 (s, 1H) 8.09 (s, 1H) 8.34 (s, 1H) 8.48 (s, 1H).

(4) N'-(2-chloro-5-(7-methyl-6-(4-pyridinyl)imidazo[1,2-a]pyridin-3-yl)-3-pyridinyl)-N,N-dimethylsulfamide. To a 5 mL microwave tube was added N-(5-(6-bromo-7-methylimidazo[1,2-a]pyridin-3-yl)-2-chloropyridin-3-yl)dimethylaminosulfonamide (0.060 g, 0.135 mmol), pyridin-4-ylboronic acid (0.020 g, 0.162 mmol), A-Phos (4.20 mg, 6.75 µmol), potassium acetate (0.033 g, 0.337 mmol), water (0.2 mL), and n-butanol (3 mL). The resulting mixture was sealed and underwent microwave heating at 100° C. for 20 min. The solvent was removed. The residue was partitioned between pH 7-buffer (1M TRIS-HCL) and DCM. The aqueous layer was extracted more with DCM (2×50 mL). The combined organic layers were dried over MgSO$_4$ and concentrated. The crude product was purified using SiO$_2$ chromatography (Teledyne Isco RediSep®, P/N 40 g SiO$_2$, DCM:MeOH=90%:5% Flow=40 mL/min). Solvent was removed in vacuo to afford the desired product as light yellow solid (15 mg). MS (ESI pos. ion) m/z: 442.9. Calcd exact mass for $C_{20}H_{19}ClN_6O_2S$: 442.1. $^1$H NMR (300 MHz, CHLOROFORM-d) δ ppm 2.36

(s, 3H) 2.81 (s, 6H) 6.92 (br. s., 1H) 7.33 (d, J=4.24 Hz, 2H) 7.66 (br. s., 1H) 7.82 (br. s., 1H) 8.13 (s, 1H) 8.18 (s, 1H) 8.35 (s, 1H) 8.73 (br. s., 2H).

Example 24

N-(2-Chloro-5-(imidazo[1,2-a]pyrimidin-3-yl)pyridin-3-yl)-4-fluorobenzenesulfonamide

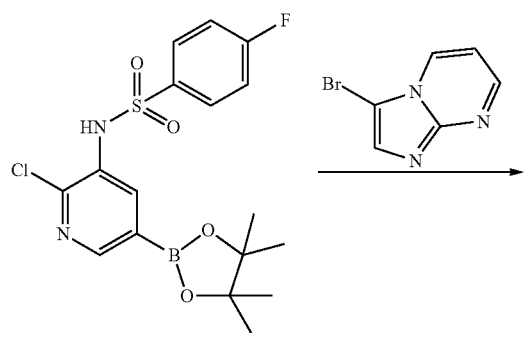

To a 50 mL round-bottomed flask was added 3-bromoimidazo[1,2-a]pyrimidine (58 mg, 291 μmol, Syntech, Houston, Tex.), N-(2-chloro-5-(4,4,5,5-tetramethyl-1,3,2-dioxaborolan-2-yl)pyridin-3-yl)-4-fluorobenzenesulfonamide (120 mg, 291 μmol), tetrakis(triphenylphosphine) palladium (34 mg, 29 μmol), aqueous sodium carbonate (2 M, 0.29 mL, 582 μmol), dioxane (3 mL). The reaction mixture was stirred at 100° C. for 5 h. The mixture was cooled down to room temperature. The reaction mixture was diluted with water (5 mL) and extracted with $CH_2Cl_2$ (5×20 mL). The organic extract was washed with saturated NaCl (5 mL), dried over $Na_2SO_4$, filtered and concentrated in vacuo and the residue was purified by silica gel chromatography, eluting with 10% MeOH/$CH_2Cl_2$ to give N-(2-chloro-5-(imidazo[1,2-a]pyrimidin-3-yl)pyridin-3-yl)-4-fluorobenzenesulfonamide (68 mg, 58% yield). MS (ESI positive ion) m/z: calcd for $C_{17}H_{11}ClFN_5O_2S$: 403.0; found: 403.9 (M+1). $^1H$ NMR (300 MHz, MeOH) δ ppm 7.23 (dd, J=6.94, 4.17 Hz, 1H) 7.25-7.36 (m, 2H) 7.84-7.94 (m, 2H) 8.04 (s, 1H) 8.28 (d, J=2.34 Hz, 1H) 8.52 (d, J=2.19 Hz, 1H) 8.70 (dd, J=4.17, 1.83 Hz, 1H) 8.94 (dd, J=6.94, 1.83 Hz, 1H)

Example 25

N-(2-Chloro-5-(6-chloroimidazo[1,2-b]pyridazin-3-yl)pyridin-3-yl)-4-fluorobenzenesulfonamide

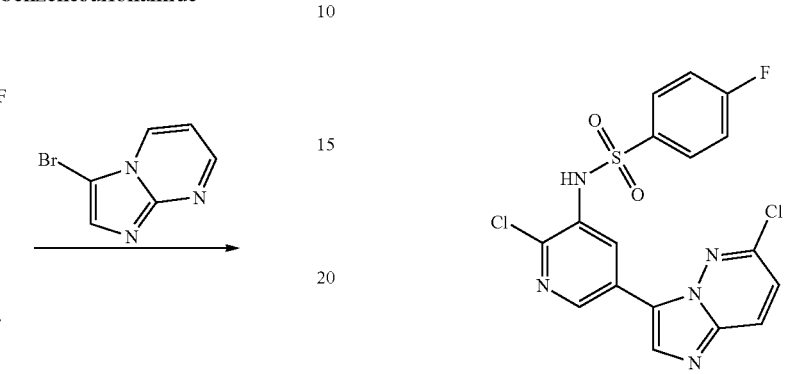

To a 10-mL, reaction vial was added 3-bromo-6-chloroimidazo[1,2-b]pyridazine (0.100 g, 0.43 mmol, Combi-Blocks, San Diego, Calif.), N-(2-chloro-5-(4,4,5,5-tetramethyl-1,3,2-dioxaborolan-2-yl)pyridin-3-yl)-4-fluorobenzenesulfonamide (0.213 g, 0.52 mmol), [1,1'-bis(diphenylphosphino)ferrocene]-dichloropalladium, complex with dichloromethane (24 mg, 0.032 mmol), sodium carbonate (0.137 g, 1.29 mmol), dioxane (2 mL) and water (1 mL). The vial was sealed and purged with nitrogen for several minutes. The reaction mixture was stirred at 100° C. for 1 h and then allowed to cool to room temperature. The organic phase was taken and the solvents eliminated under vacuum. The crude reaction mixture was purified first by silica gel chromatography (1 to 3% MeOH/$CH_2Cl_2$) followed by preparative HPLC (30-90% ACN 0.1% TFA/water 0.1% TFA) and free based by treatment with a sat aqueous solution of sodium bicarbonate and extraction with dichloromethane (3×). The combined organics were dried over $Na_2SO_4$, filtered and the solvents were eliminated under vacuum. The title compound was obtained as a white solid. MS (ESI positive ion) m/z: 438.0 (M+1). $^1H$ NMR (400 MHz, DMSO-$d_6$) δ ppm 7.43 (t, J=8.7 Hz, 2H) 7.52 (d, J=9.6 Hz, 1H) 7.86-7.94 (m, 2H) 8.36 (d, J=9.4 Hz, 1H) 8.49 (s, 1H) 8.57 (d, J=1.8 Hz, 1H) 8.89 (s, 1H) 10.52 (s, 1H).

The following assays can be used to determine the degree of activity of individual compounds as PI3 kinase and/or mTOR inhibitors.

Recombinant Expression of PI3K Enzymes

Full length p110 subunits of PI3K α, β and δ, N-terminally labeled with polyHis tag, can be co-expressed with p85 with Baculo virus expression vectors in sf9 insect cells. P110/p85 heterodimers can be purified by sequential Ni-NTA, Q-HP, Superdex-100 chromatography. Purified α, β and δ isozymes can be stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with poly-His tag, can be expressed with Baculo virus in Hi5 insect cells. The γ isozyme can be purified by sequential Ni-NTA, Superdex-200, Q-HP chromatography. The γ isozyme can be stored frozen at −80° C. in $NaH_2PO_4$, pH 8, 0.2M NaCl, 1% ethylene glycol, 2 mM β-mercaptoethanol.

|  | Alpha | Beta | Delta | Gamma |
|---|---|---|---|---|
| 50 mM Tris | pH 8 | pH 7.5 | pH 7.5 | pH 8 |
| MgCl2 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 hr | 2 hr | 2 hr | 1 hr |
| [Enzyme] | 15 nM | 40 nM | 15 nM | 50 nM |

In Vitro PI3 Kinase Enzyme Assays (PI3K ATPLoss)

PI3K enzyme assays (alpha, beta, delta and gamma) can be performed in 25 μL with the above final concentrations of components in white polyproplyene plates. Phosphatidyl inositol phosphoacceptor, PtdIns(4,5)P$_2$ (e.g., P4508) can be obtained from Echelon Biosciences, Salt Lake City, Utah. The ATPase activity of the alpha and gamma isozymes may not be greatly stimulated by PtdIns(4,5)P$_2$ under these conditions, it can be omitted from the assay of these isozymes. Test compounds can be dissolved in DMSO and diluted with three-fold serial dilutions. The compound in DMSO (1 μL) may be added per test well, and the inhibition relative to reactions containing no compound, with and without enzyme can be determined. After assay incubation at RT, the reaction can be stopped and residual ATP can be determined by addition of an equal volume of a commercial ATP bioluminescence kit (Perkin Elmer EasyLite, Perkin Elmer, Waltham, Mass.) according to the manufacturer's instructions, and detected using an Analyst GT luminometer.

Activity data for the compounds tested in the PI3Kα enzyme assay is provided in Table 1 under the column heading ATP Loss (PI3Kα).

Cell-Based Phospho-Akt Ser473Assay (HCT 116 Cell)

This assay determines the ability of a compound to inhibit the phosphorylation of Serine 473 in Akt using a MSD based sandwich immunoassay (Meso Scale Detection, Meso Scale Discovery (MSD), Gaithersburg, Md.). HCT 116 human colon carcinoma cell lines can be grown in McCoy's 5A growth medium (GIBCO, Carlsbad, Calif.) containing 10% FBS (GIBCO, Carlsbad, Calif.) and X1 Penicillin-streptomycin-glutamine (GIBCO, Carlsbad, Calif.). Prior to the assay, cells can be detached from the culture flask with trypsin, and re-suspended in complete media to give a final concentration of $1.6 \times 10^5$ cells per mL. Aliquots (100 μl) of the HCT116 cell suspension can be seeded into each well of a 96 well tissue culture plate to give a final density of 16,000 cells per well. Cells can then be incubated overnight at 37° C.

The following day the cells can be treated with serially diluted test compounds and incubated for 2 hours at 37° C. The culture media on the HCT 116 cells can be replaced with 189 μL McCoys media, supplemented with 0.1% BSA (ICN Biomedicals, Inc., Costa Mesa, Calif.). Compounds can be prepared as either 10 mM or 0.5 mM stock solutions in DMSO, and serially diluted 3 fold in a 10-point dose-response curve to give final concentrations that are 200-fold greater than the desired final test concentration. Aliquots (1 μL) of serially-diluted compounds can be transferred to 96 well tissue culture plates containing the HCT 116 cells. As a minimum response control, each plate can contain wells having a final concentration of 2.5 μM of a potent PI3K inhibitor which had previously been shown to completely inhibit Akt phosphorylation at this test concentration. As a maximum response control, wells can contain 0.5% DMSO in place of compound. The plates can be mixed at 700 rpm for 2 min to ensure even distribution of the test compound and incubated for 2 hours at 37° C. Cells can then be stimulated with insulin-like growth factor 1 (Sigma, St Louis, Mo.) at final concentration of 100 ng/ml for 15 minutes at 37° C. The media can then be removed and the cells treated with 80 μL cell-lysis buffer (MSD) containing a cocktail of protease and phosphatase inhibitors for one hour at 4° C.

25 μL Cell lysate can then be transferred to pre-blocked MSD assay plates pre-coated with a capture antibody specific for Akt, and the plates can be incubated for 2 hours at room temperature. The cell lysates can then be removed and plates can then be washed four times with 200 μl per well of Tris wash buffer (500 mM Tris, PH 7.5, 1.5 M NaCl, 0.2% Tween-20). Subsequently cells can be incubated for 1 hour at room temperature with a 25 μL solution containing the detection antibody, anti-phospho Akt (Ser 473) labeled with an electrochemiluminescent compound (Meso Scale Discovery SULPHO-TAG™ label, MSD, Gaithersburg, Md.). The detection antibody can be removed and plates can then be washed four times with 200 μL per well of Tris wash buffer. An aliquot of 150 μL of diluted MSD read buffer can then be applied to each well, and the electrochemiluminescent signal can be measured using a MSD SECTOR™ plate reader (Meso Scale Discovery, Gaithersburg, Md.). This instrument measures the intensity of emitted light to determine a quantitative measure of phosphorylated Akt in each well. The dose-response data obtained with each compound can be analyzed and the IC$_{50}$ inhibition of Akt phosphorylation at Ser473 can be calculated.

Activity data for the compounds tested in the PI3K cell based Akt assay is provided in Table 1 under the column heading HCT116 Cell.

pAkt AlphaScreen (U87 Cell)

The pAkt AlphaScreen® assay (PerkinElmer, Waltham, Mass.) determines whether there is phosphorylation of Akt at Serine 473 by recruitment of a phosphospecific antibody. This assay was performed using U87 MG cells. The U87 growth media consists of MEM (Gibco, Carlsbad, Calif.) supplemented with 10% FBS (Gibco), 1× Non-Essential Amino Acids (Gibco) and 1× Penicillin/Streptomycin/Glutamine (Gibco). The cells were maintained weekly using 0.05% Trypsin (Gibco) and replated in 150 mm TC—Treated Culture Dishes (Corning, Corning, N.Y.).

The first day of the assay, the adherent cells were trypsinized, media was added to the loose cells and cells were mixed to a homogenous mixture. 0.5 ml of the homogenous mixture was counted on the Beckman Coulter® Vi-CELL™ XR (Fullerton, Calif.). 50 frames of cells were counted and the number of viable cells was determined. The cells were then diluted to 0.25 million cells per ml, and centrifuged at 200 rcf for 5 minutes. The media was removed and the cells were reconstituted in fresh media for plating. The cells were plated at 20 μl per well on the PerkinElmer® Flexprop PLUS in Low Volume 384 Well White Tissue Culture Plates (Corning) with a final cell density of 5K cells per well. The plates were incubated overnight at 37° Celsius, 5% CO$_2$.

On the second day, the compound plates were prepared, the cells were treated with compound and the pAkt reaction mix was added to the cell lysate. 384 well compound plates were prepared containing 1 μl of compound per well starting at 5 mM and diluted 1:2 across the row, resulting in a 22 well serial dilution. 39 μl of growth media was added to the compound plate in rows 1-22 using the PerkinElmer® Flexprop PLUS resulting in a DMSO concentration of 2.5%. The cell plates and diluted compound plates were put onto the V$_{ELOC}$-ITY11™ VPREP™ 384 ST where the compound plate was mixed and 5 μl of serially diluted compound or controls was added to the cell plate. The final concentration of the compounds was 25 µM serially diluted to 11.9 pM in 0.5% DMSO. The cell plates were then incubated with compound for two hours at 37° Celsius, 5% $CO_2$. After two hours, the media in the cell plates was aspirated using the BioTek® ELx405HT plate washer (Winooski, Vt.) removing the majority of media and compound without disturbing the adherent U87 cells. The following assay reagents are components of the SureFire® Akt (Ser 473) Phosphorylation 50K Point Kit (TGR BioSciences, Adelaide, Australia) and an IgG Detection Kit (PerkinElmer, Waltham, Mass.). 5 µl of 1× Lysis Buffer was added to each well using the PerkinElmer® Flexprop PLUS. The plates were then incubated at room temperature on a shaker for ten minutes. The AlphaScreen® reaction was prepared under low light conditions (subdued or green light) including p-Akt (Ser 473) Reaction Buffer, Dilution Buffer, Activation Buffer, Acceptor Beads and Donor Beads at a ratio of 40:20:10:1:1 respectively. The AlphaScreen® reaction was added to the cell lysate at 6 µl per well using the PerkinElmer® Flexprop PLUS. The plates were placed in a humid environment to reduce edge effects and incubated overnight at room temperature with restricted air flow in the dark.

On the final day of the experiment, the plates were read on the PerkinElmer® EnVision™ 2103 Multilable Reader using the standard AlphaScreen® readout. The POC is calculated and the data is analyzed to report the $IC_{50}$ IP for pAkt at Serine 473.

Activity data for the compounds tested in the PI3K cell based Akt assay is provided in Table 1 under the column heading U87

In Vitro PI3K AlphaScreen® Assay

The PI3K AlphaScreen® assay (PerkinElmer, Waltham, Mass.) measures the activity of a panel of four phosphoinositide 3-kinases: PI3Kα, PI3Kβ, PI3Kγ, and PI3Kδ. Each of these enzymes phosphorylates the 3'-hydroxyl group on phosphatidylinositiol (4,5)-bisphosphate ($PIP_2$) to produce phosphatidylinositol (3,4,5)-trisphosphate ($PIP_3$). This phosphorylation activity is measured using a GST-tagged $PIP_3$ binding protein (Echelon Biosciences, Salt Lake City, Utah), an anti-GST-tagged Acceptor bead, and streptavidin-Donor bead. The interaction of biotinylated-$PIP_3$ analog ($IP_4$) and the $PIP_3$ binding protein brings both Acceptor and Donor beads together producing, upon excitation of the Donor beads at 680 nm, a singlet oxygen species leading to the luminescent AlphaScreen® signal. When $PIP_3$ is produced via phosphorylation of PIP2 by a PI3K, PIP3 competes with biotinylated-$PIP_3$ analog ($IP_4$) for binding to the $PIP_3$ binding protein. In the absence of this interaction, proximity of the Donor and Acceptor beads is decreased, producing a loss of luminescent signal which is inversely proportional to PI3K activity. An inhibitor reduces activity of the enzyme, resulting in less $PIP_3$ production and greater luminescence.

The enzyme reaction buffer is made using sterile water (Baxter, Deerfield, Ill.) and 50 mM Tris HCl pH 7, 14 mM $MgCl_2$, 2 mM sodium cholate, and 100 mM NaCl. 2 mM DTT is added fresh the day of the experiment. The AlphaScreen® reaction buffer is made using sterile water and 10 mM Tris HCl pH 7.5, 150 mM NaCl, 0.10% Tween 20, and 30 mM EDTA. 1 mM DTT is added fresh the day of the experiment.

The source plates for this assay are 384-well Greiner clear polypropylene plates containing test compounds at 5 mM and diluted 1:2 over 22 points. Columns 23 and 24 contain only DMSO as these are designated for positive and negative controls. Source plates are replicated into 384-well Optiplates (PerkinElmer, Waltham, Mass.), 0.5 µL/well, to make assay-ready plates.

The different PI3K isoforms are each diluted in enzyme reaction buffer to 2× working solutions. PI3Kα is diluted to 1.6 nM, PI3Kβ is diluted to 0.8 nM, PI3Kγ is diluted to 15 nM, and PI3Kδ is diluted to 1.6 nM. Two different 2× substrate solutions are made in enzyme reaction buffer. In one solution, PI(4,5)P2 (Echelon Biosciences, Salt Lake City, Utah) is diluted to 10 µM and ATP is diluted to 20 µM. This solution is used in the assays testing PI3Kα and PI3Kβ. In a second solution, PI(4,5)P2 is diluted to 10 µM and ATP is diluted to 8 µM. This solution is used in the assays testing PI3Kγ and PI3Kδ.

The AlphaScreen® reaction solutions are made using beads from the anti-GST AlphaScreen® kit (PerkinElmer, Waltham, Mass.). Two solutions are made in Alphascreen reaction buffer to 4× working concentrations. In one solution, biotinylated-$IP_4$ (Echelon Biosciences, Salt Lake City, Utah) is diluted to 40 nM and streptavadin-Donor Beads are diluted to 80 µg/mL. In the second solution, $PIP_3$-binding protein (Echelon Biosciences, Salt Lake City, Utah) is diluted to 40 nM and anti-GST-Acceptor Beads are diluted to 80 µg/mL. 10 µL/well of enzyme reaction buffer is added to Column 24 of the assay ready plates in place of enzyme. This is done for plates in the PI3Kα, β, and δ assays.

Using a 384-well dispensing Multidrop (Titertek, Huntsville, Ala.), 10 µL/well of 2× enzyme (PI3Kα, β, δ) is added to Columns 1-23 of the appropriate assay ready plates (for PI3Kγ 10 µL is added to Columns 1-24). 10 µL/well of the appropriate substrate solution (the solution with 20 µM ATP for PI3Kα and β assays, and the solution with 8 µM ATP for PI3Kγ and δ assays) is then added to Columns 1-24 of the plates. Plates are then incubated at room temperature for 20 minutes.

In the dark, 10 µL/well of the Donor Bead solution is added to Columns 1-24 of the plates to quench the enzyme reaction. The plates are incubated at room temperature for 30 minutes. Still in the dark, 10 µL/well of the Acceptor Bead solution is also added to Columns 1-24 of the plates. The plates are then incubated in the dark for 1.5 hours. The plates are read on an Envision Multilabel Plate Reader (PerkinElmer, Waltham, Mass.) with a 680 nm excitation filter and a 520-620 nm emission filter.

Activity data for the compounds tested in the assay is provided in Table 1 under the column heading PI3Kα AlphaScreen®.

The compounds of the present invention may also inhibit mTOR. The assay below can be used to determine if a compound inhibits mTOR. Thus, one aspect of the present invention concerns compounds that inhibit PI3K and mTOR. The present invention also contemplates the use of such compounds for the treatment of the diseases and conditions, such as cancer, disclosed herein.

In Vitro mTOR Assay

The Invitrogen (Carlsbad, Calif.) mammalian target of rapamycin (mTOR) Lanthascreen assay can be used to quantitate mTOR kinase activity in an in vitro setting. Active mTOR phosphorylates eukaryotic translation initiation factor 4E binding protein 1 (4E-BP1) on residue threonine 46. This phosphorylation event can be detected with a phospho-specific terbium (Tb) labeled Ab, in turn bringing the Tb label in close proximity to the GFP tagged 4E-BP 1 and allowing for time-resolved fluorescence resonance energy transfer (TR-FRET), which correlates 4E-BP1 phosphorylation levels with mTOR kinase activity.

Enzyme reaction buffer can be prepared in deionized water containing 50 mM HEPES (pH 7.5), 0.01% Polysorbate 20, 1 mM EGTA, and 10 mM $MnCl_2$.

Dilutions of the compound to be tested can be prepared in 96-well polypropylene plates (Fisher Scientific, Waltham, Mass.). One row represents a 10-point dose of compound diluted 1:3 in enzyme reaction buffer and 20% dimethyl sulfoxide (DMSO). The top concentration for all compounds is 36 µM. Wells 6 and 12 can serve as the no compound (DMSO only) and high compound controls.

An mTOR substrate solution can prepared in enzyme reaction buffer containing 1600 nM green fluorescent protein tagged eukaryotic translation initiation factor 4E binding protein 1 (GFP-4E-BP1) (Invitrogen, Carlsbad, Calif.) and 28 uM adenosine triphosphate (ATP) (Calbiochem, Gibbstown, N.J.).

mTOR enzyme (Invitrogen, Carlsbad, Calif.) can be diluted in enzyme reaction buffer to a working concentration of 100 ng/mL.

The enzyme assay can be run in 384 well low volume assay plates (Corning, Corning, N.Y.). 2.5 uL of substrate solution containing GFP-4E-BP1 and ATP can be added to appropriate wells in the assay plate followed by 2.5 µL of compound dilutions. 5 µL of appropriately diluted mTOR enzyme can be added and the reaction allowed to proceed for 1 hour at room temperature. Final reagent concentrations in the enzyme assay are 50 ng/mL mTOR, 400 nM GFP-4E-BP1, and 7 µM ATP.

The enzyme assay can be terminated upon the addition of 10 µL of 20 mM EDTA and 4 nM Tb-labeled anti-phospho-4E-BP1 [T46] antibody (Invitrogen, Carlsbad, Calif.). The assay plate can then be incubated at room temperature for 1 hour and results read on a Tecan Safire II plate reader (Tecan, Männedorf, Switzerland).

Activity data for the compounds tested in the assay is provided in Table 1 under the column heading mTOR.

TABLE 1

| Example No. | PI3Kα AlphaScreen® $K_i$ µM | PI3Kα ATPLoss $IC_{50}$ µM | mTOR $IC_{50}$ µM | U87 Cell $IC_{50}$ µM | HCT116 Cell $IC_{50}$ µM |
|---|---|---|---|---|---|
| 1 | 0.126 | 0.076 | | | |
| 2 | 1.291 | 0.931 | | | |
| 3 | 0.028 | 0.030 | 0.155 | | 0.352 |
| 4 | 0.019 | 0.013 | | | 0.180 |
| 5 | 0.020 | 0.016 | 0.848 | 1.224 | |
| 6 | 0.006 | 0.014 | 0.039 | 0.208 | |
| 7 | 0.002 | 0.005 | 0.036 | 0.042 | |
| 8 | 0.001 | 0.004 | 0.032 | 0.083 | |
| 9 | 0.004 | 0.006 | 0.364 | 0.0760 | |
| 10 | >1.500 | 15.720 | >50.000 | >25.000 | |
| 11 | 0.779 | 1.498 | 2.169 | 4.978 | |
| 12 | 0.626 | 0.861 | 3.748 | 2.193 | |
| 13 | >1.500 | 4.671 | 9.657 | >25.000 | |
| 14 | 0.268 | | 5.101 | 6.966 | |
| 15 | 0.286 | | 2.038 | 6.621 | |
| 16 | 1.077 | | 4.519 | 3.991 | |
| 17 | 0.465 | | 0.180 | | |
| 18 | 0.001 | | 0.015 | 0.007 | |
| 19 | 0.001 | | 0.015 | 0.009 | |
| 20 | 0.005 | | 0.032 | 0.032 | |
| 21 | 0.015 | | 0.258 | 0.281 | |
| 22 | 0.021 | | 0.157 | 0.168 | |
| 23 | 0.004 | | 0.018 | 0.008 | |
| 24 | 0.378 | 0.781 | >50.000 | | |
| 25 | 0.022 | 0.047 | 0.102 | | 0.564 | blank = not determined

It is noted that if an assay is run more than once the number above represents an average of the results from each experiment.

What is claimed is:

1. A compound, or a pharmaceutically acceptable salt thereof, selected from:
   4-fluoro-N-(5-imidazo[1,2-a]pyridin-3-yl-3-pyridinyl)benzenesulfonamide;
   N-(2-chloro-5-imidazo[1,2-a]pyridin-3-yl-3-pyridinyl)-4-fluorobenzenesulfonamide;
   N-(2-chloro-5-(7-methylimidazo[1,2-a]pyridin-3-yl)-3-pyridinyl)-4-fluorobenzenesulfonamide;
   N-(5-(6-bromoimidazo[1,2-a]pyridin-3-yl)-2-chloro-3-pyridinyl)-4-fluorobenzenesulfonamide;
   N-(2-chloro-5-(6-(4-pyridinyl)imidazo[1,2-a]pyridin-3-yl)-3-pyridinyl)-4-fluorobenzenesulfonamide;
   N-(2-chloro-5-(6-(3-pyridinyl)imidazo[1,2-a]pyridin-3-yl)-3-pyridinyl)-4-fluorobenzenesulfonamide;
   N-(2-chloro-5-(6-(4-morpholinyl)imidazo[1,2-a]pyridin-3-yl)-3-pyridinyl)-4-fluorobenzenesulfonamide;
   3-(5,6-dimethoxy-3-pyridinyl)imidazo[1,2-a]pyridine;
   6-bromo-3-(5,6-dimethoxy-3-pyridinyl)imidazo[1,2-a]pyridine;
   3-(5,6-dimethoxy-3-pyridinyl)-6-(4-pyridinyl)imidazo[1,2-a]pyridine;
   3-(3-(5,6-dimethoxy-3-pyridinyl)imidazo[1,2-a]pyridin-6-yl)-1,3-oxazolidin-2-one;
   (4R)-4-benzyl-3-(3-(5,6-dimethoxy-3-pyridinyl)imidazo[1,2-a]pyridin-6-yl)-1,3-oxazolidin-2-one;
   (4S)-4-benzyl-3-(3-(5,6-dimethoxy-3-pyridinyl)imidazo[1,2-a]pyridin-6-yl)-1,3-oxazolidin-2-one;
   3-(5,6-dimethoxy-3-pyridinyl)-6-(4-morpholinyl)imidazo[1,2-a]pyridine;
   N'-(2-chloro-5-(6-(4-pyridinyl)imidazo[1,2-a]pyridin-3-yl)-3-pyridinyl)-N,N-dimethylsulfamide;
   N'-(2-chloro-5-(6-(2-(trifluoromethyl)-4-pyridinyl)imidazo[1,2-a]pyridin-3-yl)-3-pyridinyl)-N,N-dimethylsulfamide;
   N-(2-chloro-5-(7-(3-pyridinyl)imidazo[1,2-a]pyridin-3-yl)-3-pyridinyl)methanesulfonamide;
   N'-(2-chloro-5-(7-(4-pyridinyl)imidazo[1,2-a]pyridin-3-yl)-3-pyridinyl)-N,N-dimethylsulfamide;
   N'-(2-chloro-5-(7-(3-pyridinyl)imidazo[1,2-a]pyridin-3-yl)-3-pyridinyl)-N,N-dimethylsulfamide; or
   N'-(2-chloro-5-(7-methyl-6-(4-pyridinyl)imidazo[1,2-a]pyridin-3-yl)-3-pyridinyl)-N,N-dimethylsulfamide.

2. A pharmaceutical composition comprising: a compound in accordance with claim 1, or a pharmaceutically acceptable salt thereof; and a pharmaceutically acceptable excipient.

* * * * *